(12) United States Patent
Sugiyama et al.

(10) Patent No.: US 11,097,009 B2
(45) Date of Patent: Aug. 24, 2021

(54) CTB-PI POLYAMIDE CONJUGATE FOR ACTIVATING EXPRESSION OF SPECIFIC GENE

(71) Applicant: KYOTO UNIVERSITY, Kyoto (JP)

(72) Inventors: Hiroshi Sugiyama, Kyoto (JP); Toshikazu Bando, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 289 days.

(21) Appl. No.: 15/549,487

(22) PCT Filed: Feb. 12, 2016

(86) PCT No.: PCT/JP2016/054162
§ 371 (c)(1),
(2) Date: Aug. 8, 2017

(87) PCT Pub. No.: WO2016/129680
PCT Pub. Date: Aug. 18, 2016

(65) Prior Publication Data
US 2019/0255182 A1 Aug. 22, 2019

(30) Foreign Application Priority Data
Feb. 12, 2015 (JP) .............................. JP2015-025715

(51) Int. Cl.
| | |
|---|---|
| *A61K 31/167* | (2006.01) |
| *A61K 47/59* | (2017.01) |
| *C07D 207/34* | (2006.01) |
| *A61K 31/787* | (2006.01) |
| *C07D 403/14* | (2006.01) |
| *A61K 45/00* | (2006.01) |

(52) U.S. Cl.
CPC .......... *A61K 47/595* (2017.08); *A61K 31/167* (2013.01); *A61K 31/787* (2013.01); *A61K 45/00* (2013.01); *C07D 207/34* (2013.01); *C07D 403/14* (2013.01)

(58) Field of Classification Search
CPC ............................ A61K 47/595; A61K 31/167
See application file for complete search history.

(56) References Cited

U.S. PATENT DOCUMENTS

| | | | | |
|---|---|---|---|---|
| 2006/0167107 A1* | 7/2006 | Kundu | .................. | C07C 235/64 514/617 |
| 2007/0191260 A1 | 8/2007 | Sugiyama et al. | | |
| 2011/0160399 A1* | 6/2011 | Nagase | .................. | A61K 45/06 525/54.1 |
| 2016/0310605 A1 | 10/2016 | Nagase et al. | | |

FOREIGN PATENT DOCUMENTS

| | | |
|---|---|---|
| EP | 2 311 494 | 4/2011 |
| WO | 98/49142 | 11/1998 |
| WO | 2005/087762 | 9/2005 |
| WO | 2005/112924 | 12/2005 |
| WO | 2010/001933 | 1/2010 |
| WO | 2013/160885 | 10/2013 |
| WO | WO-2015027243 A2 * | 2/2015 ......... A61K 47/6923 |
| WO | 2015/053413 | 4/2015 |

OTHER PUBLICATIONS

Han et al. Angew. Chem. Int. Ed. 2015, 54, 8700-8703 (Year: 2015).*
International Search Report dated Apr. 12, 2016 in International Application No. PCT/JP2016/054162.
International Preliminary Report on Patentability dated Apr. 12, 2016 in International Application No. PCT/JP2016/054162.
Sean D. Taverna et al., "How chromatin-binding modules interpret histone modifications: lessons from professional pocket pickers", Nature Structural Molecular Biology, Nov. 2007, vol. 14, No. 11, p. 1025-1040.
Tony Kouzarides, "Chromatin Modifications and Their Function", Cell 128, Feb. 23, 2007, p. 693-705.
Gordin Zupkovitz, et al., "Negative and Positive Regulation of Gene Expression by Mouse Histone Deacetylase", Molecular and Cellular Biology, Nov. 2006, vol. 26, No. 21, p. 7913-7928.
Peter B. Dervan, "Molecular Recognition of DNA by Small Molecules", Bioorganic & Medicinal Chemistry 9 (2001) p. 2215-2235.
Peter B. Dervan et al., "Recognition of the DNA minor groove by pyrrole-imidazole polyamides", Current Opinion in Structural Biology 2003, 13:284-299.
Peter B. Dervan et al., "Programmable DNA Binding Oligomers for Control of Transcription", Curr. Med. Chem.—Anti-Cancer Agents, 2005, 5, p. 373-387.
K. Mantelingu et al., "Activation of p300 Histone Acetyltransferase by Small Molecules Altering Enzyme Structure: Probed by Surface-Enhanced Raman Spectroscopy", J. Phys. Chem., B 2007, 111, p. 4527-4534.
Hiroshi Sugiyama, "Activation of specific genes by pyrrole-imidazolepolyamide having histone deacetylase inhibitory activity", Research Reports of the Uehara Memorial Foundation, vol. 23 (2009), pp. 1-5, with English translation.
Extended European Search Report dated Jun. 22, 2018 in European Patent Application No. 16749323.8.
Liu et al., "Suberoylanilide Hydroxamic Acid Induces Akt-mediated Phosphorylation of p300, Which Promotes Acetylation and Transcriptional Activation of RelA/p65", The Journal of Biological Chemistry, 2006, vol. 281, No. 42, pp. 31359-31368.

(Continued)

Primary Examiner — Matthew P Coughlin
(74) Attorney, Agent, or Firm — Wenderoth, Lind & Ponack, L.L.P.

(57) ABSTRACT

The present invention provides: a histone modification control agent for activating expression of a specific gene, i.e., a complex including a histone acetylation enzyme activator useful as an agent for activating a specific gene, and a polyamide for recognizing a regulatory region of a target gene; and a method for manufacturing the same. This complex specifically activates a group of genes relating to maintenance and/or differentiation of stem cells or precursor cells.

5 Claims, 7 Drawing Sheets
Specification includes a Sequence Listing.

(56) References Cited

OTHER PUBLICATIONS

Han et al., "A Synthetic DNA-Binding Domain Guides Distinct Chromatin-Modifying Small Molecules to Activate an Identical Gene Network". Angewandte Chemie International Edition, 2015, vol. 54, pp. 8700-8703.
European Communication pursuant to Article 94(3) EPC dated Jun. 14, 2019 in corresponding European Patent Application No. 16749323.8.
Communication pursuant to Article 94(3) EPC dated May 29, 2020 in corresponding European Patent Application No. 16749323.8.
Office Action dated Nov. 24, 2020 in corresponding Japanese Application No. 2016-574864, with English translation, 9 pages.

* cited by examiner

Connective tissue disorder-related gene group

Cancer- and cardiovascular disease-related gene group

Pluripotency-related gene group

Fig. 8

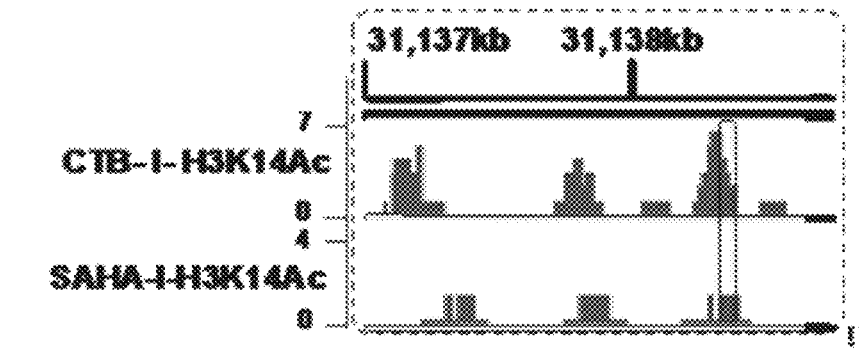

DNA sequence:
ATGATGTATAAACGGAGCACACAGCCAGGCACT........GTGGACCACAATTGCCAG
CCATTATCATTCAAGGCTCAGCAGTGACCTCCTGCGAAGAGGTTGGGGCTTCTCGGT
CACTCCAGAAACCAGTCACACCTTTCTGTGAGGTCTCAAGGCTTAGTATTTAATCTC
TAATTGCTTACACTTGTCGCCTTGAAGGACTGGAAGATACATCTTTAATAGTCCTCA
GCAGGGCTGGATGCCTTCAATCCCGCAGCAGCTCTATATTTGCAAATGGCCT
GGAGAAATCTCTCACCATTTTTCTTGTTTACAACT........TGAGGCT
GAAGTCAATCAAAATCCAGCTTTCTACAAGGGGTGCCAGGGTGTGCACC
TTAACACAGTGGCCAGTCATTGGCCTGAGGCAGAGATCCGGGAAGACA
AGCCCTATACTTGACTGGAGGTAAACCCAGCTCACAACGCGCACACACA
CAGCCCAAACAGGAC........CAGAAACGAGTCACACCCTAGACTTTCAGGAA
CAATAATCCTGGAATGAGCACTGTTTTTACCCTCAGGCTATGCTTAACCCTAAGGCC
AAAATCTTGGGTCTGATAAGGGTCAAATTTTCAAGCAGGACTAAGGGTGGGAAAAGG
GGCTC........CCCAAGCTGGGTCTGGTGCTGGGCCAGTAATGAGTGACCAGACC
CTGGGCAGGCCTAGGAGATGTGAGAGACCCTGACAAGGGCTGGGCCAGAGCAAAGGC
CAGCCTGGGCCAGCTTCCGACTCTCCCAGGCTGCTCTGCCCTCACCGGCAGT
TGTCTCTTCGAAATCCAGCTTCCACTTCCCACCTGGCCCCTGCCTGCCA
GGGCTGCCAGCAGTTGATACACACCCCTCCCTGGCCAGGGCAGCTGACC
CTGCCTGCTCCTCTCCTGGGTGCCAGGTCTGGGCAGCTGCAGGTGACCA
CTTCCCCATCAGGCTGCCCTGTCATGACCACCTCCCCACACCCCAACCC
CGTCGAAGCTCACTTGCCTCCTCCGGGTTTTGCTCCAGCTTCTCCTTCTCCAGCTT
CACGGCACCAGGGGTGACGGTGCAGGGCTCCGGGGAGGCCCCATCGGAGTTGCTCTC
CACCCCGACTCCTGCTTCGCCCTCAGGCTGAGAGGTCTCCAAGCCGCCTTGGGGCAC
TAGCCCCACTCCAACCTGGGGCCCACAGTACGGCATCCCCCACAGAACTCATA
CGGCGGGGGGCATGGGGGAATCCCCCACACCTCAGAGCCTGGCCCAACC
CCCGGCCCGATTCCTGGCCCTCCAGGAGGGC........CTTAGCCAGG
TCCGAGGATCAACCCAGCCCGGCTCCGGCCCCCTGGCCCATCACCTCC
ACCACCTGGAGGGGGCGAGAAGGCGAAATCCGAAGCCAGGTGTCCCGCC
ATGGG........GGCGCCCCAAGCCGGGGGCCTGGTGAAATGAGGGCTT
GCGAAGGGACTACTCAACCCCTCTCT

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
tgataaaccg agagggaagc                                           20

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
tgtgaattcc actggttctc c                                             21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
agccctcatt tcaccaggcc                                               20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
tgggactcct ccgggttttg c                                             21

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 5
gggaaatggg aggggtgcaa aagagg                                        26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 6
ttgcgtgagt gtggatggga ttggtg                                        26

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
attccactgc tctccttgag                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer
```

```
<400> SEQUENCE: 8
gtgaacccaa ccatctgtgt                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
ggtgagatgc atagggaact                                               20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 10
aagccagttt caagctgc                                                 18

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 11
aatacctcag cctccagcag atg                                           23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 12
tgcgtcacac cattgctatt cttc                                          24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
ctagctactt gctgtttccc                                               20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 14
ccacgttcac tcccatgtt                                                19
```

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
tgaaccaccc agggaatga                                                  19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
gaagtcttct gaaggcacag                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 17
gggtacctgc tgtgtgaaac aa                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 18
cctccactga aacatggaag ca                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: probe

<400> SEQUENCE: 19
accacagtcc atgccatcac                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 20
tccaccaccc tgttgctgta                                                 20

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: promotor
```

<400> SEQUENCE: 21 aaggaa                                                                    6

<210> SEQ ID NO 22
<211> LENGTH: 1501
<212> TYPE: DNA
<213> ORGANISM: Artificial Sequence
<220> FEATURE:
<223> OTHER INFORMATION: Description of Artificial Sequence: promotor

<400> SEQUENCE: 22

```
atgatgtata aacggagcac acagccaggc acttaggaag tggaccacaa ttgccagcca      60
ttatcattca aggctcagca gtgacctcct gcgaagaggt tggggcttct cggtcactcc     120
agaaaccagt cacaccttc tgtgaggtct caaggcttag tatttaatct ctaattgctt      180
acacttgtcg ccttgaagga ctggaagata catctttaat agtcctcagc agggctggat    240
gccttcaatc ccgcagcagc tctatatttg caaatggcct ggagaaatct ctcaccattt    300
ttcttgttta caactttgga actgaggctg aagtcaatca aaatccagct ttctacaagg    360
ggtgccaggg tgtgcacctt aacacagtgg ccagtcattg gcctgaggca gagatccggg    420
gaagacaagc cctatacttg actggaggta acccagctc acaacgcgca cacacacagc     480
ccaaacagga gatcctatca gaaacgagtc acaccctaga ctttcaggaa caataatcct    540
ggaatgagca ctgttttac cctcaggcta tgcttaaccc taaggccaaa atcttgggtc     600
tgataagggt caaattttca agcaggacta agggtgggaa aaggggctca aaccaacccc    660
aagctgggtc tggtgctggg ccagtaatga gtgaccagac cctgggcagg cctaggagat    720
gtgagagacc ctgacaaggg ctgggccaga gcaaaggcca gcctgggcca gcttccgact    780
ctcccaggct gctctgccct caccggcagt tgtctcttcg aaatccagct tccacttccc    840
acctggcccc tgcctgccag ggctgccagc agttgataca cacccctccc tggccagggc    900
agctgaccct gcctgctcct ctcctgggtg ccaggtctgg gcagctgcag gtgaccactt    960
ccccatcagg ctgccctgtc atgaccacct ccccacaccc caaccccgtc gaagctcact   1020
tgcctcctcc gggttttgct ccagcttctc cttctccagc ttcacggcac cagggtgac    1080
ggtgcagggc tccggggagg ccccatcgga gttgctctcc accccgactc ctgcttcgcc   1140
ctcaggctga gaggtctcca agccgccttg gggcactagc cccactccaa cctggggccc   1200
acagtacgcc atcccccac agaactcata cggcggggg catgggggaa tcccccacac     1260
ctcagagcct ggcccaaccc ccggcccgat tcctggccct ccaggagggc cttggaagct   1320
tagccaggtc cgaggatcaa cccagcccgg ctccggcccc cctggcccat cacctccacc   1380
acctggaggg ggcgagaagg cgaaatccga agccaggtgt cccgccatgg ggaaggaagg   1440
cgccccaagc cggggggcctg gtgaaatgag ggcttgcgaa gggactactc aacccctctc   1500
t                                                                  1501
```

<210> SEQ ID NO 23
<211> LENGTH: 6
<212> TYPE: DNA
<213> ORGANISM: Artificial Sequence
<220> FEATURE:
<223> OTHER INFORMATION: Description of Artificial Sequence: promotor

```
<400> SEQUENCE: 23 taggaa                                                                    6

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: promotor

<400> SEQUENCE: 24 ttggaa                                                                    6

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: promotor

<400> SEQUENCE: 25 atccta                                                                    6

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence: promotor

<400> SEQUENCE: 26 aaccaa                                                                    6

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: promotor

<400> SEQUENCE: 27 ttggaa                                                                    6

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence: promotor

<400> SEQUENCE: 28 aaggaa                                                                    6
```

CTB-PI POLYAMIDE CONJUGATE FOR ACTIVATING EXPRESSION OF SPECIFIC GENE

TECHNICAL FIELD

The present invention relates to a conjugate comprising a histone acetyltransferase (abbreviated to "HAT") activator and a polyamide for recognizing a regulatory region of a target gene. More specifically, the present invention relates to a conjugate comprising a benzamide compound represented by formula (I) and pyrrole imidazole polyamide (abbreviated to "PIP").

BACKGROUND ART

Molecular targeting treatment, which is a treatment method of performing treatment by using a certain molecule as a target and controlling its functions, is currently receiving attention widely. Such molecular targeting treatment targets a gene or a protein present on the surface of cells of a disease (e.g., cancer cells) and can thereby decrease the attack to normal cells by drugs so that adverse reactions can be reduced.

The eukaryotic genomes constitute chromatin (chromosomes) and are thereby packed into the nucleus. The chromatin structure is formed by the repeat of nucleosome structures constituted by DNA and histones. In recent years, the chromatin has been found to be also deeply involved in a control mechanism called epigenetics (Non Patent Literature 1). The epigenetics refer to a control mechanism that regulates transcriptional activation, etc. by acquired modification without involving change in the sequence of DNA. Among others, modification in histones which are major proteins constituting the nucleosomes has significant influence on transcription and replication or repair.

It is also considered that large change in genome-wide gene expression which is accurately regulated by epigenetic information is involved in the reprogramming of cells. Some small molecules have been known so far to artificially induce epigenetic modification (Non Patent Literatures 2 and 3).

PIP is an artificial small molecule developed with an antibiotic distamycin as a motif and reportedly binds in a sequence-specific manner to a minor group of double-stranded DNA, and there are many reports as to research on the silencing of a gene having a target sequence by PIP (Non Patent Literatures 4, 5, and 6). Furthermore, PIP is under research as a drug for kidney damage, an anticancer agent, or a therapeutic drug for corneal trauma, hypertrophic scar, bone disease, and the like by animal experiments using mice. Also, PIP is an organic small molecule expected to produce various research achievements in such a way that the induction of iPS cells by PIP has been researched in recent years at the Institute for Integrated Cell-Material Sciences (iCeMS), which is the iPS cell project of the Kyoto University, as a part of research on iPS cells.

Examples of the features of PIP include: (1) PIP can be designed to target an arbitrary gene sequence; (2) its ability to bind to DNA is stronger than that of a transcription factor; (3) PIP is taken up into the nuclei of cells without any vector or drug delivery system (DDS); (4) PIP is stable in cells or organisms without being decomposed by a nucleolytic enzyme and excreted as an undecomposed product by urinary bile; and (5) PIP can be easily modified at its N and C termini and is capable of forming conjugates with various functional small molecules.

Pyrrole imidazole (abbreviated to "PI") polyamide recognizes a base pair CG by a P/I pair, AT or TA by a P/P pair, and GC by an I/P pair and is thereby capable of binding to various arbitrary double-stranded DNAs in a sequence-specific manner. PIP bound with the target gene has been studied as a gene switch that inhibits the binding of a transcription factor to DNA and silences the particular gene.

The present inventors have successfully completed inventions relating to: an indole derivative for alkylating a particular base sequence of DNA by utilizing a PIP structure with high sequence recognition specificity and synthesizing a conjugate of an alkylating functional group and PIP (Patent Literature 1); and an alkylating agent, wherein PIP is designed to specifically bind to a gene mutation site of a driver oncogene, and the alkylating agent is bonded to the designed PIP to thereby perform alkylation targeting the gene mutation of the driver oncogene (Patent Literature 2).

Also, an invention relating to a target gene-specific histone modification-controlling agent prepared by synthesizing a conjugate of a histone modification-controlling agent and PIP (Patent Literature 3) has been successfully completed. This literature has reported that some pluripotency genes in mouse embryonic fibroblasts can be activated by epigenetic change by use of suberoylanilide hydroxamic acid (abbreviated to "SAHA") which is a histone deacetylase (abbreviated to "HDAC") inhibitor modifying chromatin.

Meanwhile, one type of benzylamide compound, which is N-(4-chloro-3-(trifluoromethyl)phenyl)-2-ethoxybenzamide (referred to as "CTB"), has been known in recent years as a compound activating histone acetyltransferase (HAT) (Non Patent Literature 7). A HAT activator differs in mechanism of action from the HDAC inhibitor described above from the viewpoint of histone modification and can therefore activate a different particular gene. It is also expected that the HAT activator can activate a particular gene synergistically or cooperatively by combination with the HDAC inhibitor. However, any conjugate of the HAT activator combined with PIP or the like has not yet been known. Furthermore, the influence of epigenetic control thereof on gene expression has not been known.

CITATION LIST

Patent Literatures

Parent Literature 1: International Publication No. WO 2005/087762
Patent Literature 2: International Publication No. WO 2015/053413
Patent Literature 3: International Publication No. WO 2010/001933

Non Patent Literatures

Non Patent Literature 1: Nat. Struct. Mol. Biol., 2007, 14, 1025-1040
Non Patent Literature 2: Cell, 2007, 128, 693-705
Non Patent Literature 3: Mol. Cell Biol., 2006, 26, 7913-7928
Non Patent Literature 4: Bioorg. Med. Chem. 2001, 9, 2215-2235
Non Patent Literature 5: Curr. Opin. Struct. Biol. 2003, 13, 284-299
Non Patent Literature 6: Curr. Med. Chem.: Anti-Cancer Agents 2005, 5, 373-387
Non Patent Literature 7: J. Phys. Chem., B 2007, 111, 4527-4534

SUMMARY OF INVENTION

Technical Problem

Thus, the present inventors have conducted intensive studies and consequently found out that: a conjugate of a histone acetyltransferase activator combined with a polyamide for recognizing a regulatory region of a target gene can be produced; and the conjugate can activate the expression or the particular gene. Particularly, it has been found out that: a conjugate comprising CTB or its derivative benzylamide compound as the HAT activator and PI polyamide as the polyamide can be produced; and the conjugate can specifically activate a group of genes are involved in cell control, for example, tumor suppressor genes, genetic disease suppressor genes, genes encoding nerve cell-controlling substances, cystic fibrosis suppressor genes, gastrointestinal disease suppressor genes, viral disease suppressor genes, or genes that is involved in the maintenance and/or differentiation of stem cells or progenitor cells. Accordingly, the present invention provides a conjugate useful as an activator of a particular gene, the conjugate comprising a histone acetyltransferase activator and a polyamide for recognizing a regulatory region of a target gene, and a method for producing the same. The present invention also provides a pharmaceutical composition, for example, a pharmaceutical composition for the treatment of cancer, and a kit for treatment or for research reagents, comprising the conjugate.

Solution to Problem

The present invention provides the following aspects, though the present invention is not limited thereto.

Conjugate

Item [1] A conjugate comprising a histone acetyltransferase activator and a polyamide for recognizing a regulatory region of a target gene.

Item [2] The conjugate according to [1], wherein the histone acetyltransferase activator is a compound represented by formula (I):

[Chem. 1]

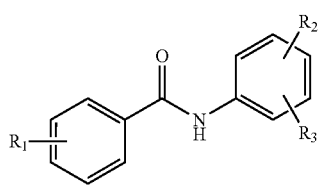

(I)

wherein
R$_1$ is an alkoxy group,
R$_2$ is an alkyl trihalide group, and
R$_3$ is a halogen atom, a cyano group, or a nitro group.

Item [3] The conjugate according to [1] or [2], wherein the histone acetyltransferase activator is a compound selected from the group consisting of the following formulae:

[Chem. 2]

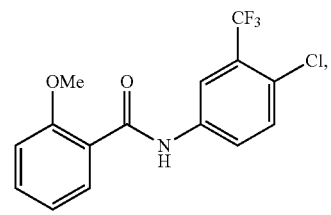

-continued

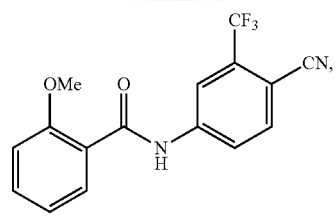

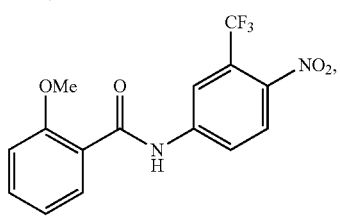

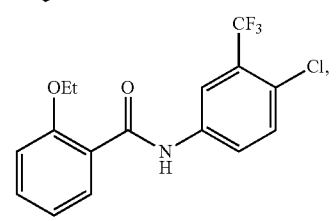

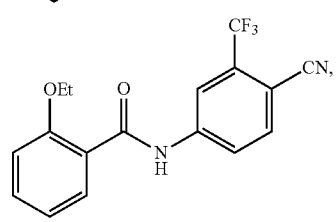

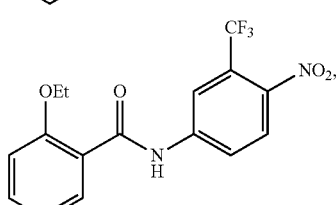

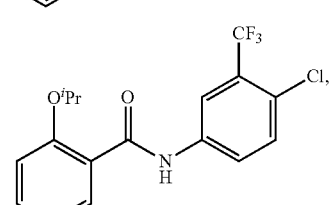

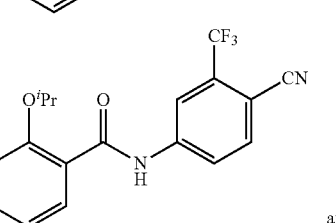

and

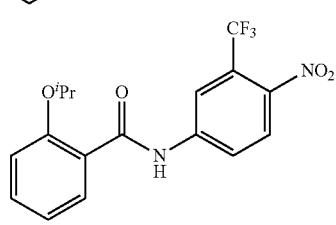

Item [4] The conjugate according to any one of [1] to [3], wherein the polyamide for recognizing a regulatory region of a target gene is pyrrole imidazole polyamide (PIP) or a modified form thereof.

Item [5] The conjugate according to any one of [1] to [4], wherein the target gene is a gene that is involved in cell control.

Item [6] The conjugate according to [5], wherein the gene that is involved in cell control is a gene that is involved in the maintenance and/or differentiation of stem cells or progenitor cells.

Item [7] The conjugate according to [6], wherein the gene that is involved in the maintenance and/or differentiation of stem cells or progenitor cells is LIF (leukemia inhibitory factor) gene, OCT-3/4 gene, NANOG gene, SOX2 gene, SALL4 gene, ZIC3 gene, LIN28B gene, EPCAM gene, DPPA4 gene, KLF4 gene, MYC gene, MYCN gene, p16INK4a (CDKN2A) gene, or MIR302C gene.

Item [8] The conjugate according to [5], wherein the gene that is involved in cell control is a tumor suppressor gene or a viral disease suppressor gene.

Item [3] The conjugate according to any one of [1] to [8], wherein the conjugate is selected from the group consisting of compounds represented by the formulae:

[Chem. 3]

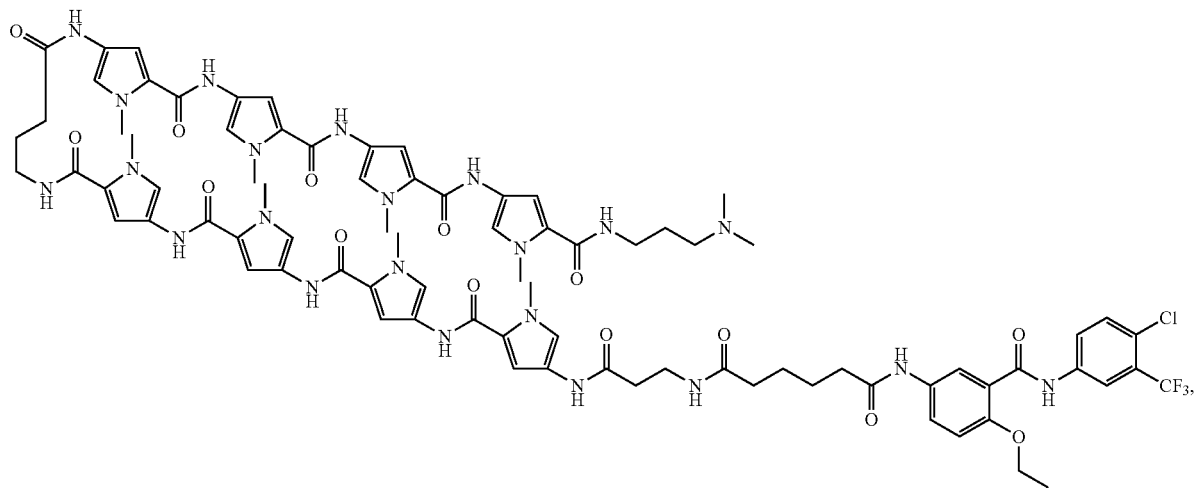

CTB-PIP-A

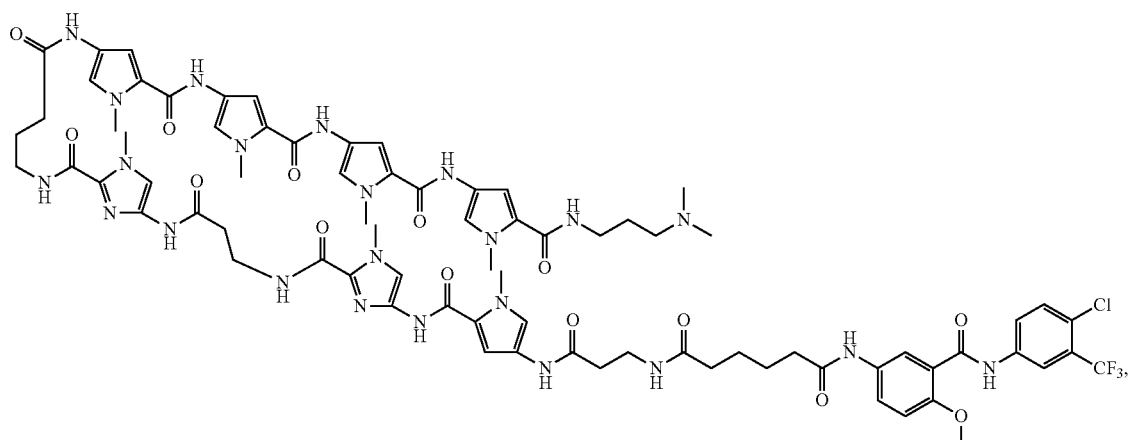

CTB-PIP-G

-continued
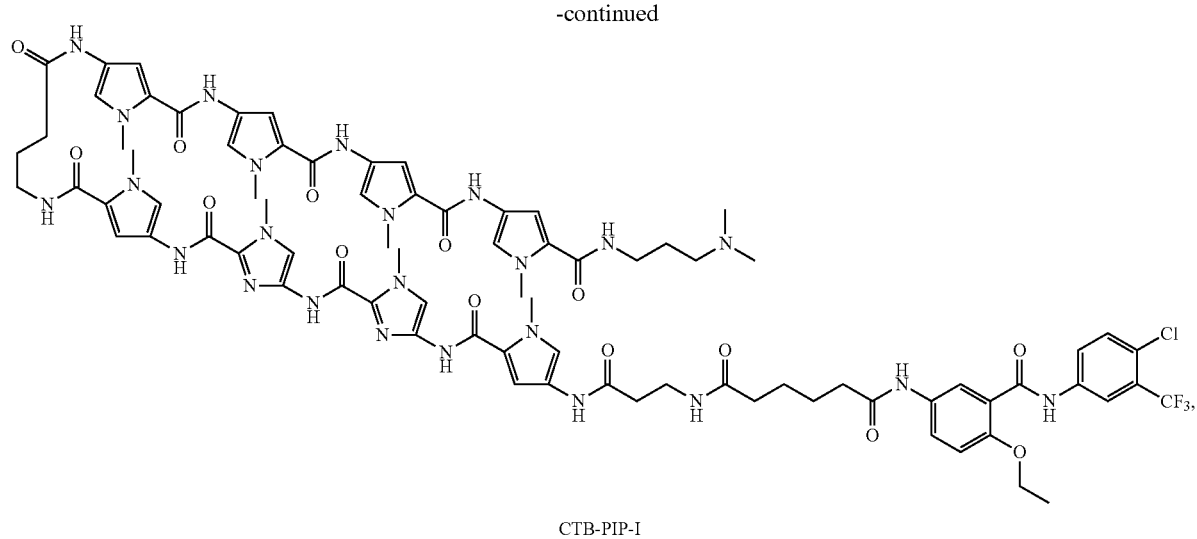
CTB-PIP-I
[Chem. 4]
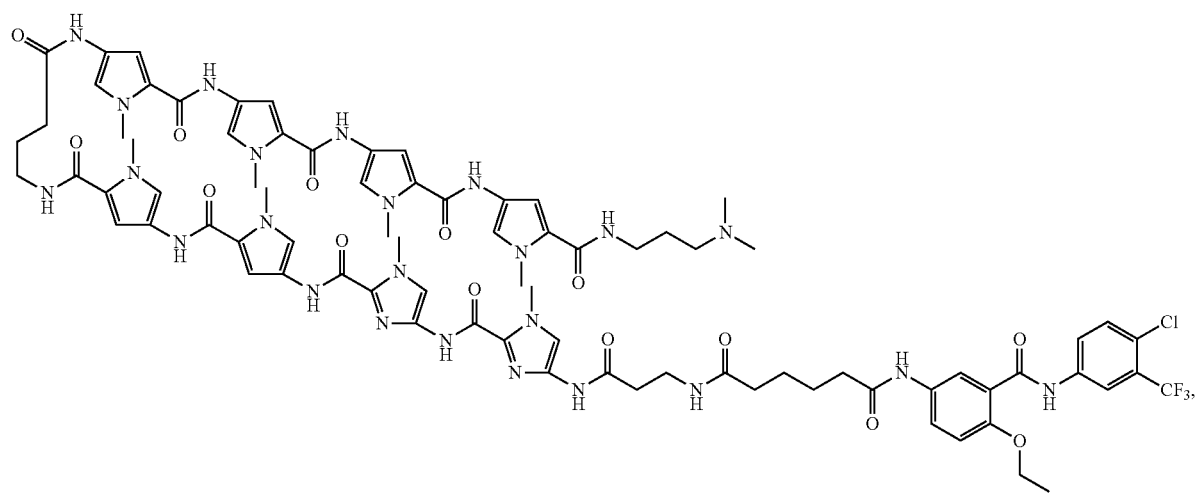
CTB-PIP-K
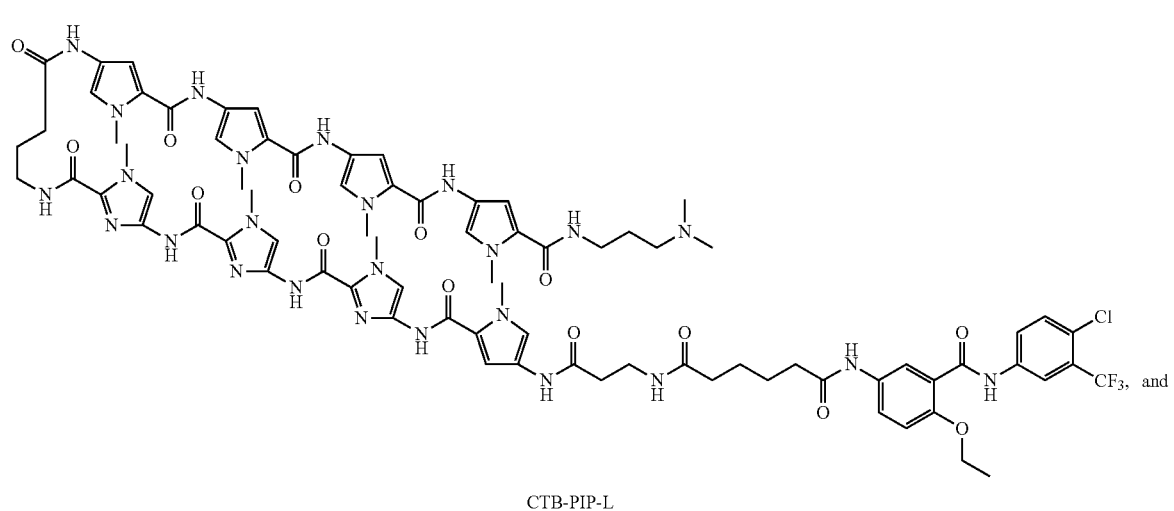
CTB-PIP-L

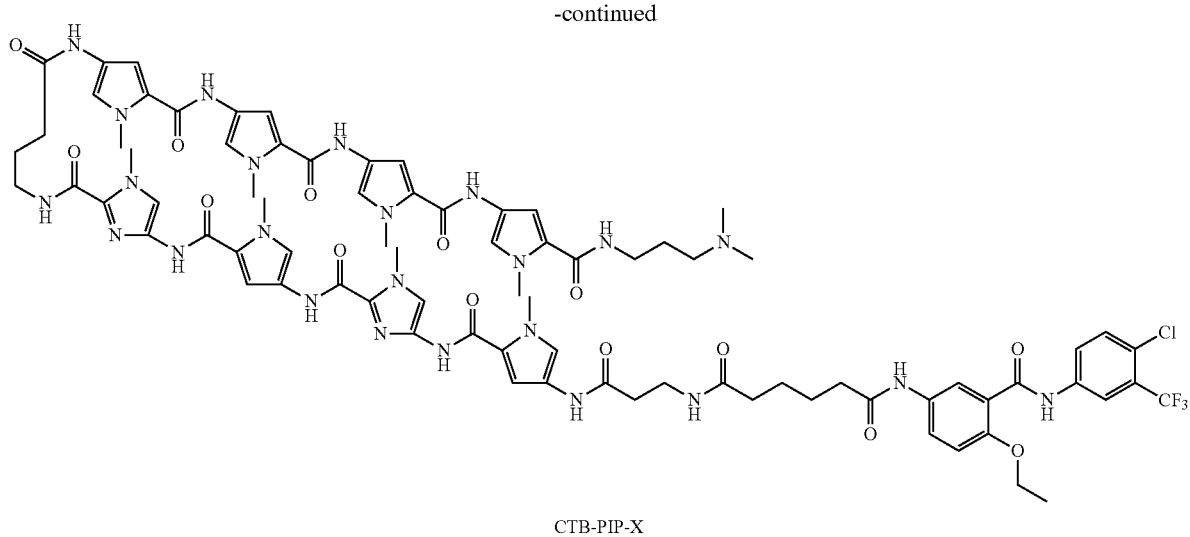

CTB-PIP-X

Use

Item [10] A target gene-specific histone modification-controlling agent comprising a conjugate according to any one of [1] to [9].

Item [11] A pharmaceutical composition comprising the conjugate according to any one of [1] to [9].

Item [12] The target gene-specific histone modification-controlling agent according to [10] or the pharmaceutical composition according to [11] for the prevention, treatment, or diagnosis of cancer or viral disease.

Item [13] A kit for prevention, treatment, or diagnosis or for research reagents, comprising the conjugate according to any one of [1] to [9].

Item [14] The kit according to [13] for the prevention, treatment, or diagnosis of cancer or viral disease.

Item [15] A method for preventing, treating, or diagnosing cancer or viral disease using the target gene-specific histone modification-controlling agent according to [10] or the pharmaceutical composition according to [11].

Item [16] Use of the conjugate according to any one of [1] to [9] in the production of a medicament for the prevention, treatment, or diagnosis of cancer or viral disease.

Method for Producing Conjugate

Item [17] A method for producing the conjugate according to any one of [1] to [9], comprising:

1. (a) preparing an amino derivative of a benzamide compound represented by formula (I)':

[Chem. 5]

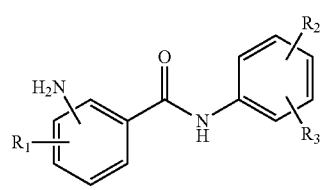

(I)' wherein $R_1$, $R_2$, $R_3$, and m are as defined in [1], which is a HAT activator;

(b) optionally, as needed, reacting a monoalkyl ester compound of an alkenyldicarboxylic acid represented by formula (III):

[Chem. 6]

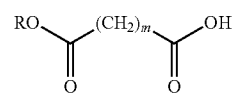

(III)

wherein R is a protective group for the carboxyl group, and m is any integer of 1 to 6,
as a partial structure of a linker
with the compound obtained in (a) to bind the same to the derivative of the formula (I)', and performing hydrolysis reaction to produce a compound (IV) represented by formula (IV):

[Chem. 7]

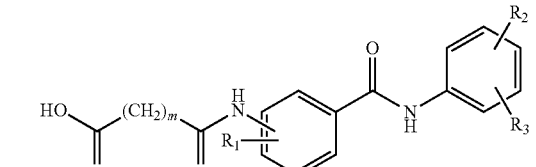

(IV)

wherein $R_1$, $R_2$, $R_3$, and m are as defined above;

2. binding the obtained compound (IV) to pyrrole imidazole polyamide (PIP) having $L_3$:

[Chem. 8]

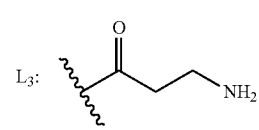

or a modified form thereof by a solid-phase synthesis technique in the presence of a coupling agent, followed by excision from the solid phase using a reagent to obtain a crude conjugate; and 3. optionally, purifying the crude conjugate.

Item [18] The production method according to [17], wherein the compound of formula (IV) is represented by the formula:

[Chem. 9]

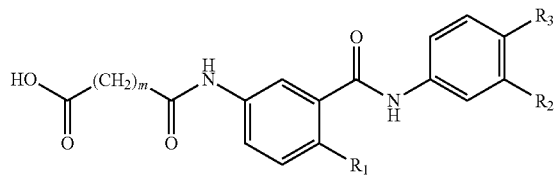

Effects of Invention

The conjugate of the present invention comprising a histone acetyltransferase activator and a polyamide for recognizing a regulatory region of a target gene can specifically activate a group of genes that are involved in cell control (e.g., tumor suppressor genes, genetic disease suppressor genes, genes encoding nerve cell-controlling substances, cystic fibrosis suppressor genes, gastrointestinal disease suppressor genes, viral disease suppressor genes, or genes are involved in the maintenance and/or differentiation of stem cells or progenitor cells). The degree of the activation is remarkably high and is as remarkably high as that of, for example, an existing SAHA-PI polyamide conjugate (Japanese Patent No. 4873510). In addition, the so-called CTB-PI polyamide of the present invention can be produced by a convenient and inexpensive production method.

BRIEF DESCRIPTION OF DRAWINGS

FIG. 8 is a drawing showing the sequence of the Oct-3/4 gene promoter region. The 6 nucleotide sequences boxed in the drawing are nucleotide sequences that were commonly recognized by SAHA-PIP-I and CTB-PIP-I.

DESCRIPTION OF EMBODIMENTS

Figure 1:
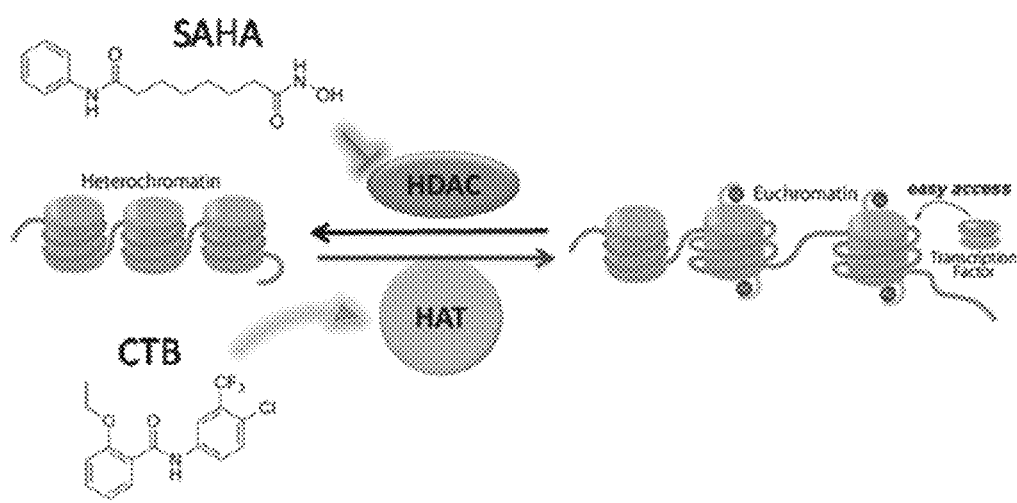
FIG. 1 is a drawing illustrating the respective structures of a histone deacetylase (HDAC) inhibitor SAHA and a histone acetyltransferase (HAT) activator CTB and the mechanism of action on a histone. SAHA and HAT respectively act on different target enzymes so that the chromatin structure is relaxed to allow easy access of a transcription factor, thereby epigenetically elevating the expression of the related gene.
Figure 2:
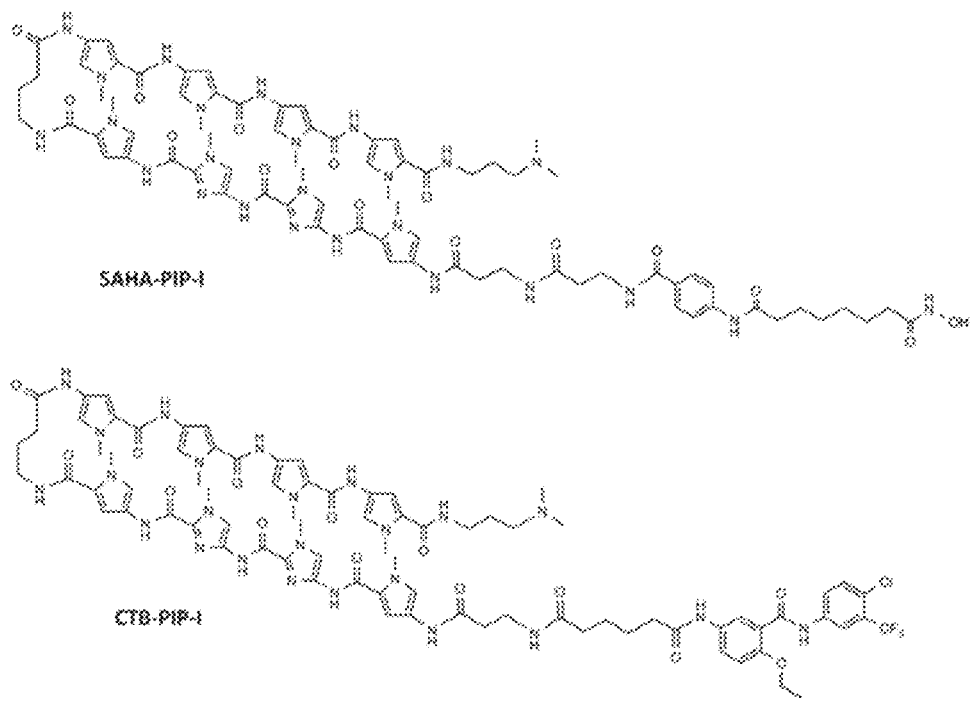
FIG. 2 is a drawing showing the comparison between the structural formulae of SAHA-PIP-I and CTB-PIP-I.

Hereinafter, the present invention is described in more detail.
(Definition)
Hereinafter, the terms used in the present specification and the claims is defined. All publications cited herein are incorporated herein by reference.
1. Histone Acetyltransferase (HAT) Activator The histone acetyltransferase (abbreviated to "HAT") of the present invention is an enzyme that highly acetylates histone proteins and participates in the activation of transcription. The histone acetylation adds negatively charged acetyl groups to histone proteins so that the histones are negatively charged to weaken the interaction between the histones and between DNA and the histones, thereby promoting dissociation. Therefore, nucleosome condensation is relaxed. It is considered that, as a result, condensation is also relaxed in a gene regulatory region to allow the binding of a transcription factor to the regulatory region, thereby promoting the expression of the gene.

The histone acetyltransferase activator means a molecule that activates acetylation caused by the histone acetyltransferase. Current examples of the histone acetyltransferase activator are only those reported by J. Phys. Chem., B 2007, 111, 4527-4534 (the above-mentioned Non Patent Literature 7), though the histone acetyltransferase activator is not limited thereto.

One specific form of the histone acetyltransferase activator of the present invention includes a benzamide compound represented by the formula (I):

[Chem. 10]

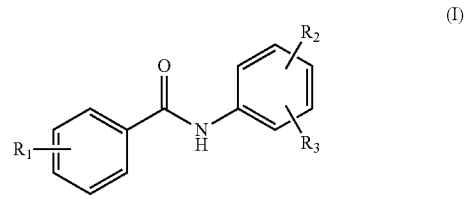

wherein
$R_1$ is an alkoxy group,
$R_2$ is an alkyl trihalide group, and
$R_3$ is a halogen atom, a cyano group, or a nitro group.
In the formula (1), $R_3$ is an electron-withdrawing group and is particularly preferably a halogen atom.

The term "alkoxy group" means a group in which an alkyl group having 1 to 6, preferably 1 to 4, more preferably 1 to 3 carbon atoms is bonded to an oxygen atom. The alkoxy group can specifically include, but is not limited to, methoxy, ethoxy, n-propoxy, isopropoxy, n-butoxy, t-butoxy, n-pentyloxy, and n-hexyloxy, and the like. Methoxy, ethoxy, or isopropoxy is more preferred, and ethoxy is still more preferred.

The term "alkyl trihalide" means a group in which an alkyl group having 1 to 3, preferably 1 or 2, more preferably 1 carbon atom(s) is substituted by 3 halogen atoms (more preferably fluorine atoms). Specific examples thereof include, but are not limited to, trifluoromethyl, trichloromethyl, 1,1,1-trifluoroethyl, and 1,1,2-trifluoroethyl. Trifluoromethyl or trichloromethyl is more preferred, and trifluoromethyl is still more preferred.

Examples of the term "halogen atom" include a fluorine atom, a chlorine atom, a bromine atom, and an iodine atom. A fluorine atom or a chlorine atom is more preferred, and a chlorine atom is still more preferred.

The substituent $R_1$ may be at an ortho position, a meta position, or a para position with respect to the carboxamide group and is preferably at an ortho position. The substituent $R_2$ may be at an ortho position, a meta position, or a para position with respect to the amide group and is preferably at a meta position. The substituent $R_3$ may be at an ortho position, a meta position, or a para position with respect to the amide group and is preferably at a para position. It is also preferred that the substituent $R_2$ and the substituent $R_3$ should be present at adjacent positions to each other.

In a preferred embodiment, the histone acetyltransferase activator of the present invention is represented by formula (II):

[Chem. 11]

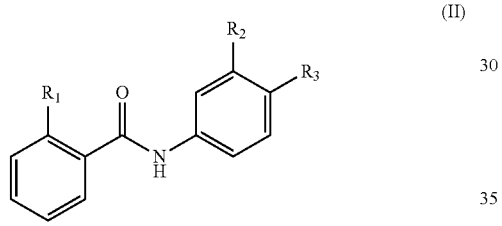

(II)

Substituents in the formula (I) and the formula (II) include compounds described below.

$R_1$ is an alkoxy group having 1 to 4 carbon atoms, $R_2$ is an alkyl trihalide having 1 carbon atom, and $R_3$ is a halogen atom.

Examples of specific compounds are shown below, though the compound of the present invention is not limited thereto.

[Chem. 12]

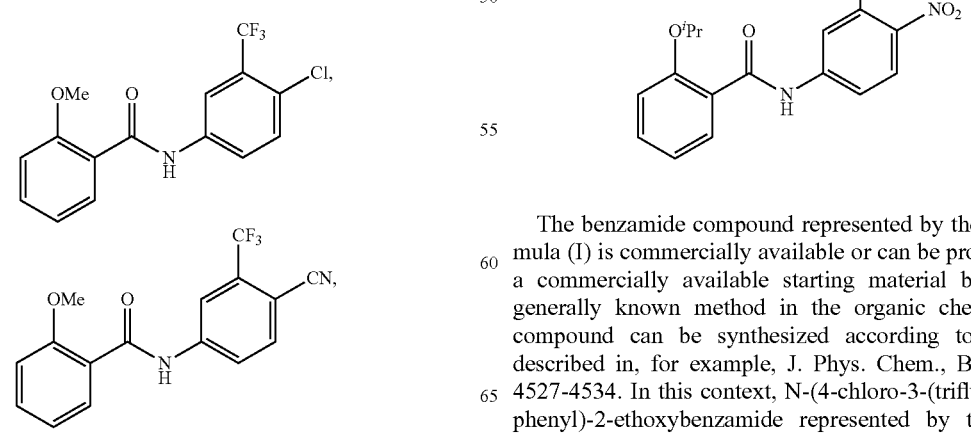

The benzamide compound represented by the above formula (I) is commercially available or can be produced from a commercially available starting material by use of a generally known method in the organic chemistry. The compound can be synthesized according to a method described in, for example, J. Phys. Chem., B 2007, 111, 4527-4534. In this context, N-(4-chloro-3-(trifluoromethyl)phenyl)-2-ethoxybenzamide represented by the formula given below is also abbreviated to "CTB" herein. Accordingly, the benzamide compound represented by the above formula (I) may be also referred to as a CTB derivative.

2. Polyamide for Recognizing Regulatory Region of Target Gene

The "polyamide for recognizing a regulatory region of a target gene" which is a component of the conjugate of the present invention means a polyamide designed to recognize the regulatory region of the target gene. In this context, the phrase "recognizing a regulatory region of a target gene" means that the target-recognizing polyamide binds (e.g., by a hydrogen bond or cross-linking), for example, to the regulatory region of the target gene and/or the neighborhood thereof. Examples of the polyamide can include DNA-binding compounds such as pyrrole polyamide (PIP) (PIP compounds including a cyclic structure, a hairpin structure, and a tandem form in which hairpin structures are connected), peptide nucleic acid (PNA), bridged nucleic acid, locked nucleic acid (LNA), and complexes such as DNA-binding protein complexes (e.g., zinc finger).

The bridged nucleic acid or the locked nucleic acid (LNA) can be designed to recognize the regulatory region of the target gene and synthesized as 2',4'-BNA in which an oxygen atom at position 2' and a carbon atom at position 4' of RNA are bridged via a methylene chain, or as 2',4'-ENA (ethylene-bridged nucleic acid) in which an oxygen atom at position 2' and a carbon atom at position 4' of RNA are bridged via an ethylene chain. LNA is also available from Proligo LLC.

The "pyrrole imidazole polyamide (referred to as PIP)" of the present invention is a polyamide containing a N-methylpyrrole unit (Py), a N-methylimidazole unit (Im), and a γ-aminobutyric acid moiety, and Py, Im, and the γ-aminobutyric acid moiety are linked to each other via an amide bond (—C(=O)—NH—) (Trauger et al., Nature, 382, 559-61 (1996); White et al., Chem Biol., 4, 569-78 (1997); and Dervan, Bioorg. Med. Chem., 9, 2215-35 (2001)). PIP is wholly folded into a U-shaped conformation (hairpin form) by the γ-aminobutyric acid moiety serving as a linker (γ-linker). In the U-shaped conformation, two chains containing Py and Im are arranged in parallel, flanking the linker. When a pair of Py and Im between these two chains is a particular combination (Py/Im pair, Im/Py pair, Py/Py pair, or Im/Im pair), this pair can bind to a particular base pair in DNA with high affinity. For example, the Py/Im pair can bind to a C-G base pair, and the Im/Py pair can bind to a G-C base pair. Also, the Py/Py pair can bind to both an A-T base pair and a T-A base pair (White et al., Chem. Biol., 4, 569-78 (1997); and Dervan, Bioorg. Med. Chem., 9, 2215-35 (2001)). PIP may additionally contain 3-hydroxypyrrole (Hp) or β alanine. As for Hp, a Hp/Py pair can bind to a T-A base pair finite et al., Nature, 391, 468-71 (1998)). The γ-linker may have a side chain having an amino group, such as N-α-N-γ-aminobutyric acid and N-β-N-γ-aminobutyric acid, which may be modified with a molecule such as FITC or biotin. Also, PIP may be modified at its N terminus with not only an acetyl group but a molecule such as FITC or biotin. β alanine/β alanine can bind to a T-A base pair or an A-T base pair. Accordingly, PIP recognizing the regulatory region of the target gene can be designed by changing, for example, the pairing combination of Py and Im according to the DNA sequence of the target. A design method and a production method for PIP are known in the art (e.g., Japanese Patent No. 3045706, Japanese Patent Laid-Open No. 2001-136974, WO03/000683, Japanese Patent Laid-Open No. 2013-234135, and Japanese Patent Laid-Open No. 2014-173032).

A modified form of PIP modified to maintain or improve the ability to bind to DNA is also included in the present invention. Examples of the modified form of PIP include a modified form containing an amine added to position α or β of the γ-aminobutyric acid of PIP, a modified form having a substituted side chain of N-α-N-γ-aminobutyric acid or N-β-N-γ-aminobutyric acid, modified forms derived from the modified forms described above by modification with a molecule such as FITC or biotin, a modified form of PIP modified at its N terminus with a molecule such as FITC or biotin, and a modified form of PIP modified at its C terminus with a molecule such as isophthalic acid.

Examples of PIP include, but are not limited thereto, compounds represented by the following formulae:

[Chem. 13]

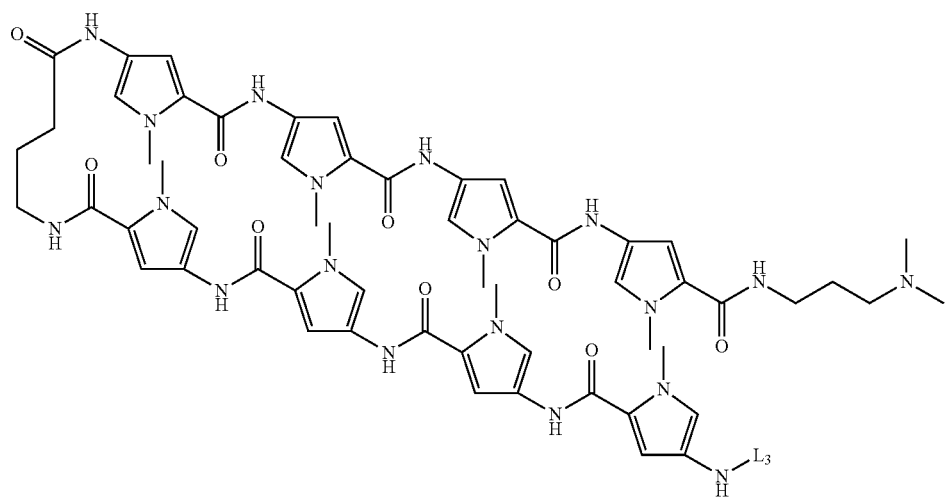

A

-continued
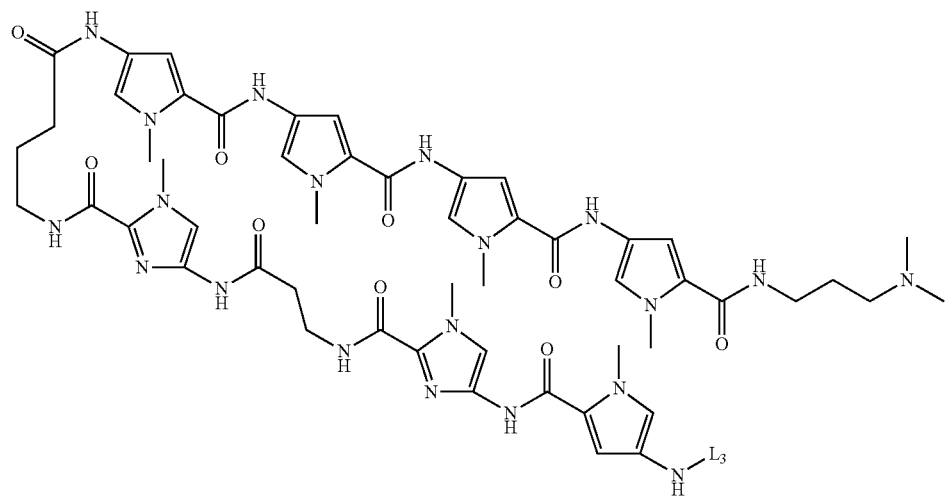
G
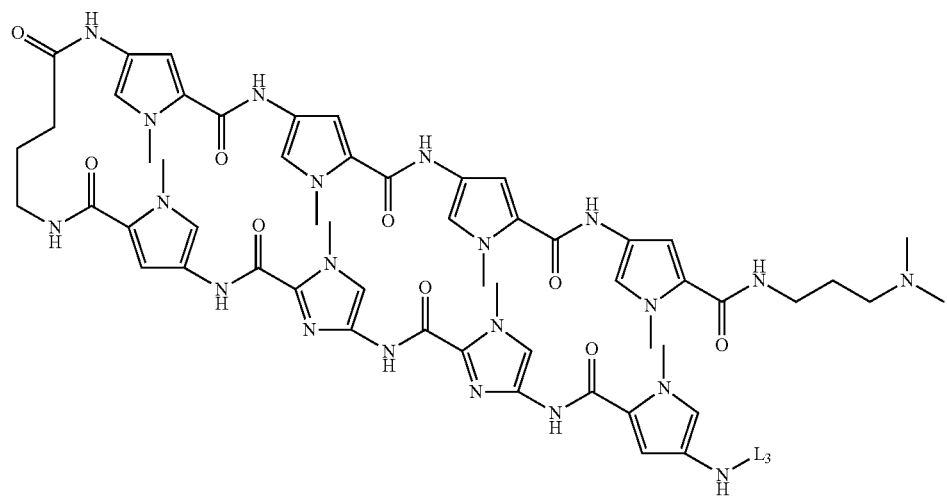
I
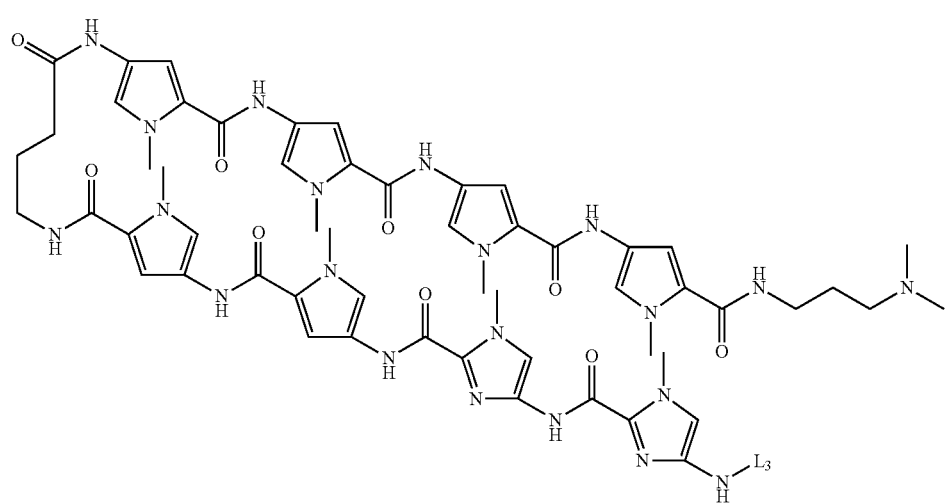
K

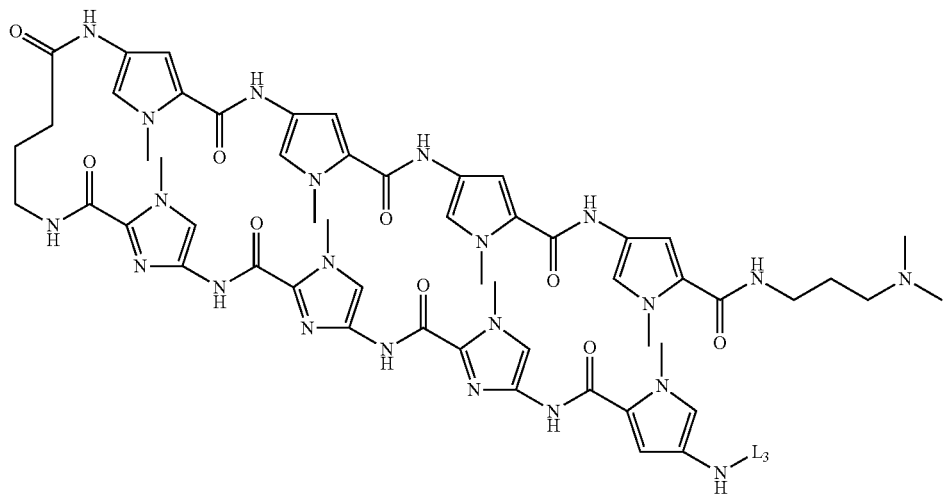

L

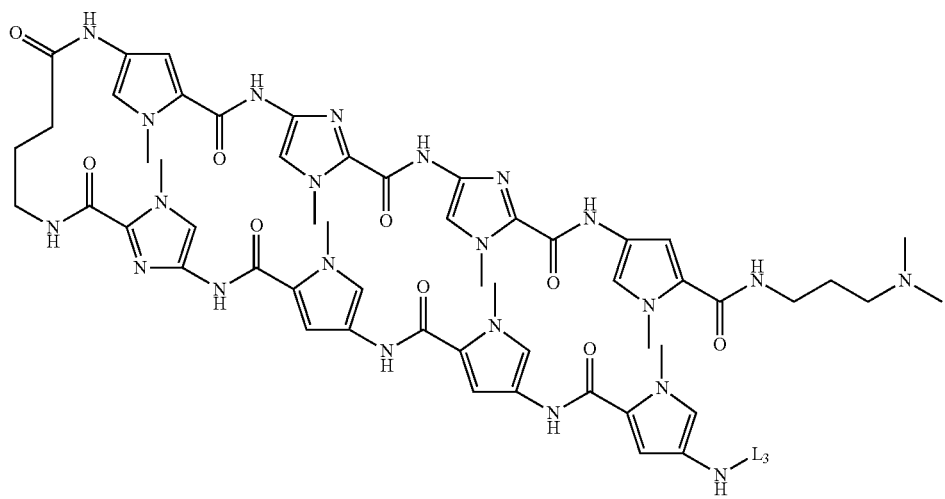

X

[Chem. 14]

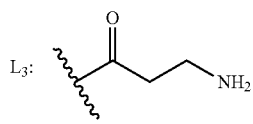

3. Conjugate

The conjugate of the present invention can be synthesized, for example, by bonding the histone acetyltransferase (HAT) activator with the polyamide for recognizing a regulatory region of a target gene. The synthesis method can be performed by, for example, a method known in the art (J. Am. Chem. Soc. 1995, 117, 2479-2490). In this context, the "bonding" pattern may be a direct bond or may be mediated by a linker. The linker is not particularly limited as long as the linker neither interferes with the action of the HAT activator nor interferes with the recognition of a site in the target gene. Examples thereof can include bonds themselves such as an amide bond, an ester bond, a phosphodisulfide bond, a coordination bond, and an ether bond, and molecules containing functional groups that form one or more types of these bonding patterns. An amide bond or a molecule that forms an amide bond is preferred.

In one embodiment, the linker is represented by the formula $L_1$:

[Chem. 15]

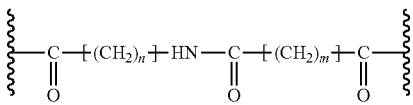

wherein m and n are each independently an integer of 1 to 6. For example, m and n are each independently preferably an integer of 1 to 4.

In the linker moiety represented by the formula $L_1$, for example, the rightmost position is linked to the histone acetyltransferase (HAT) activator, whereas the leftmost position is linked to the polyamide. The linking positions may be reversed.

In the case of linking to the histone acetyltransferase (HAT) activator, the linker is bonded to the amino (—NH$_2$) group on the benzene ring, and one typical form of the bonding pattern is shown below.

[Chem. 16]

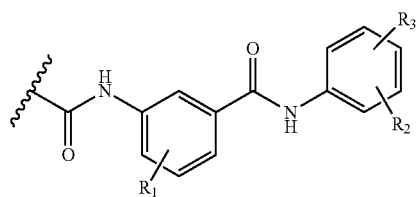

In the case of linking to PIP, the linker is bonded to the amino (—NH$_2$) group on the terminal pyrrole or imidazole ring of PIP, and one typical form of the bonding pattern is shown below.

[Chem. 17]

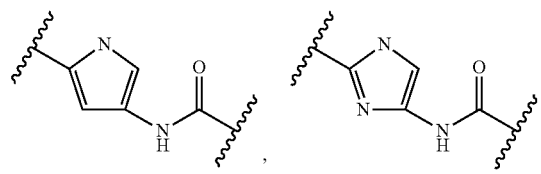

In a typical embodiment, the linker is represented by the formula $L_2$:

[Chem. 18]

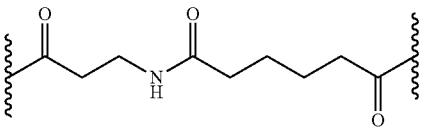

Examples of the partial structure of the linker include a moiety represented by the formula $L_3$:

[Chem. 19]

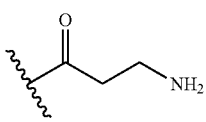

Examples of the partial structure of the linker also include a moiety represented by the formula $L_4$:

[Chem. 20]

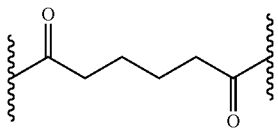

One example of PIP having the linker for linking to the HAT activator is shown below.

[Chem. 21]

PIP-1

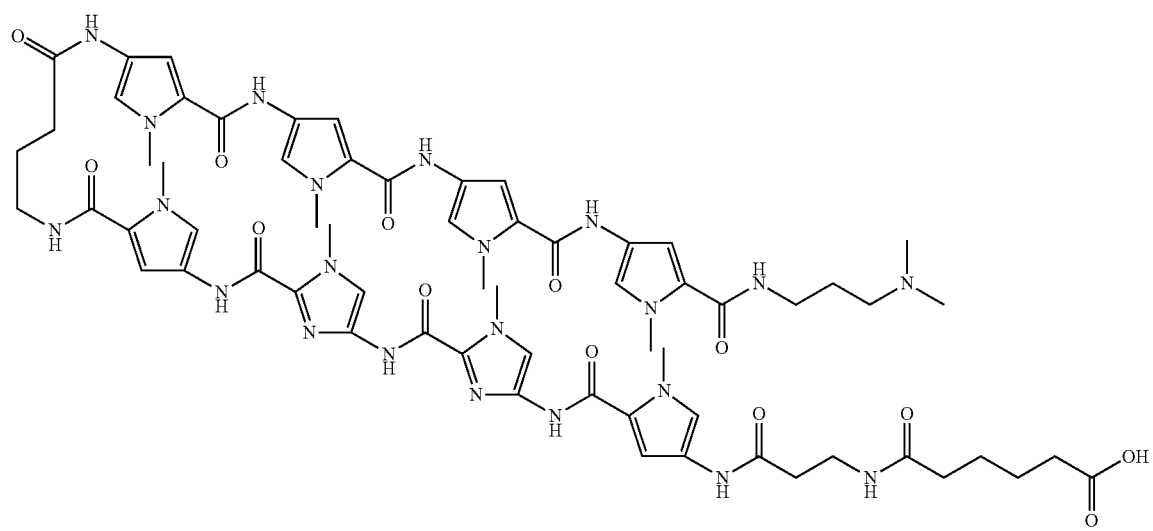

The "regulatory region of the target gene" that is recognized by the target-recognizing polyamide of the present invention is, for example, a promoter, an enhancer, a repressor, or an insulator and is preferably a promoter. The gene regulatory region and/or the neighborhood thereof to which the target-recognizing polyamide binds is preferably linker DNA (histone-unbound DNA region in a nucleosome).

Typical examples of the conjugate of the present invention are shown in the following formulae, though the conjugate of the present invention is not limited thereto.

[Chem. 22]

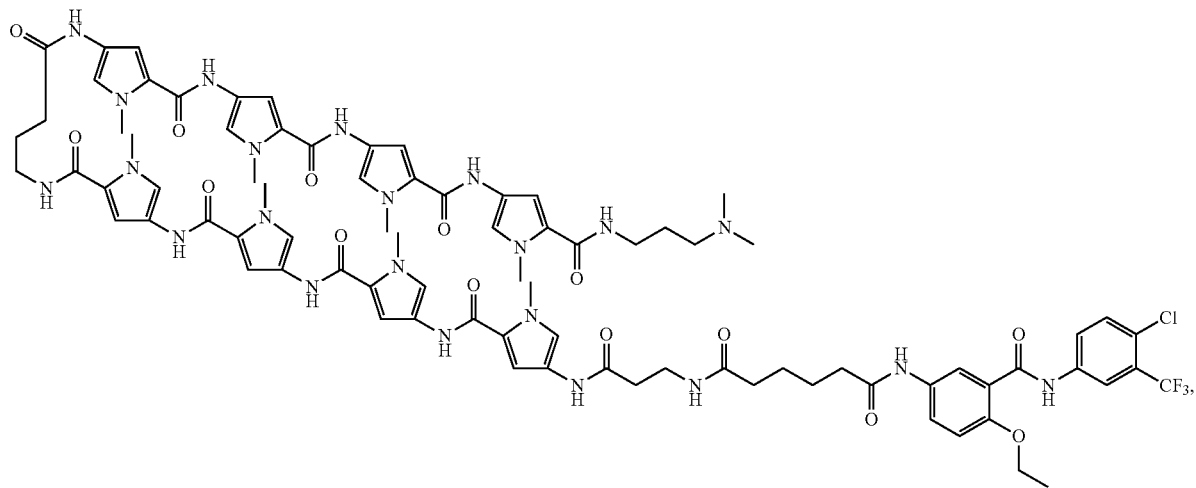

CTB-PIP-A

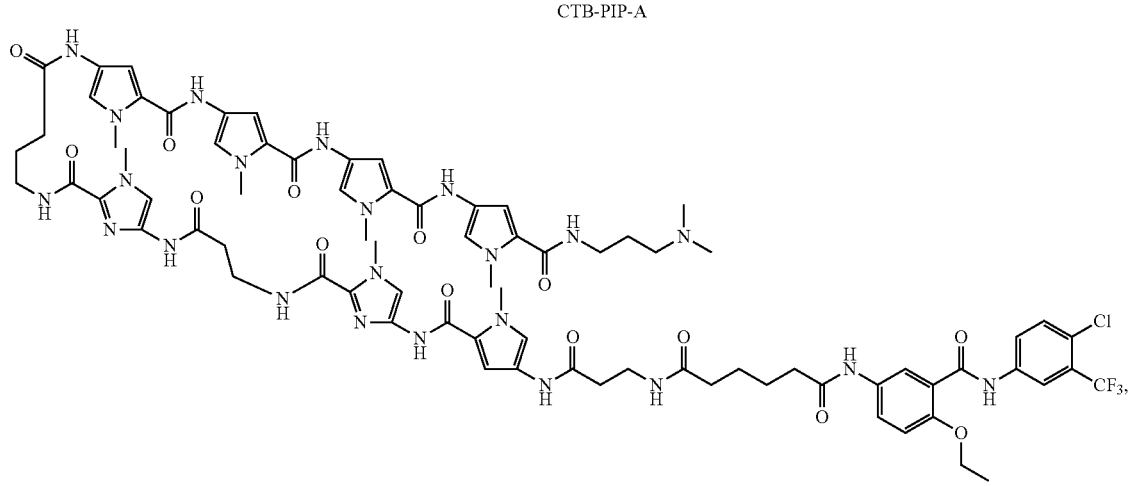

CTB-PIP-G

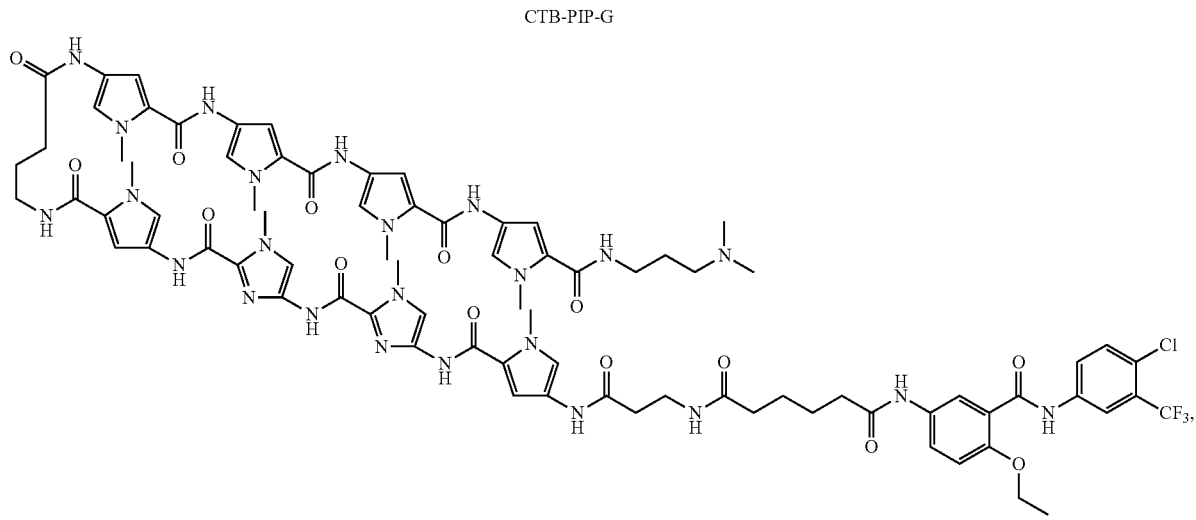

CTB-PIP-I

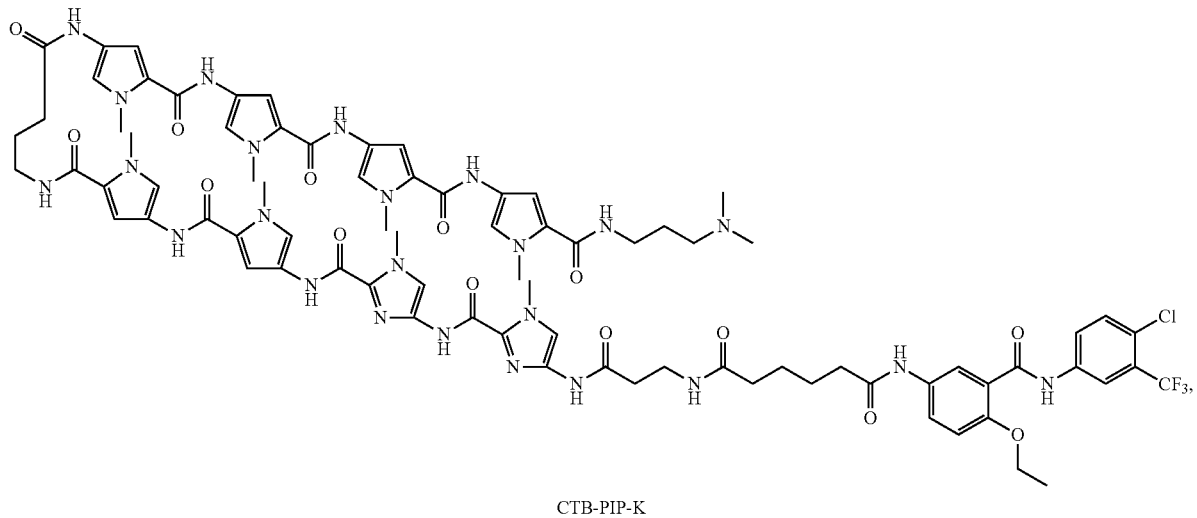
CTB-PIP-K
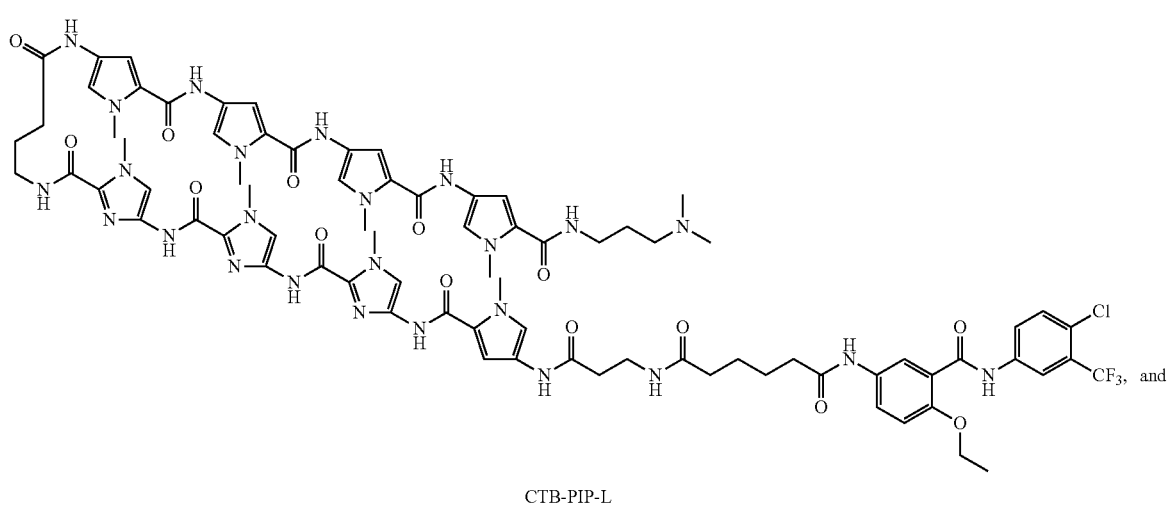
CTB-PIP-L
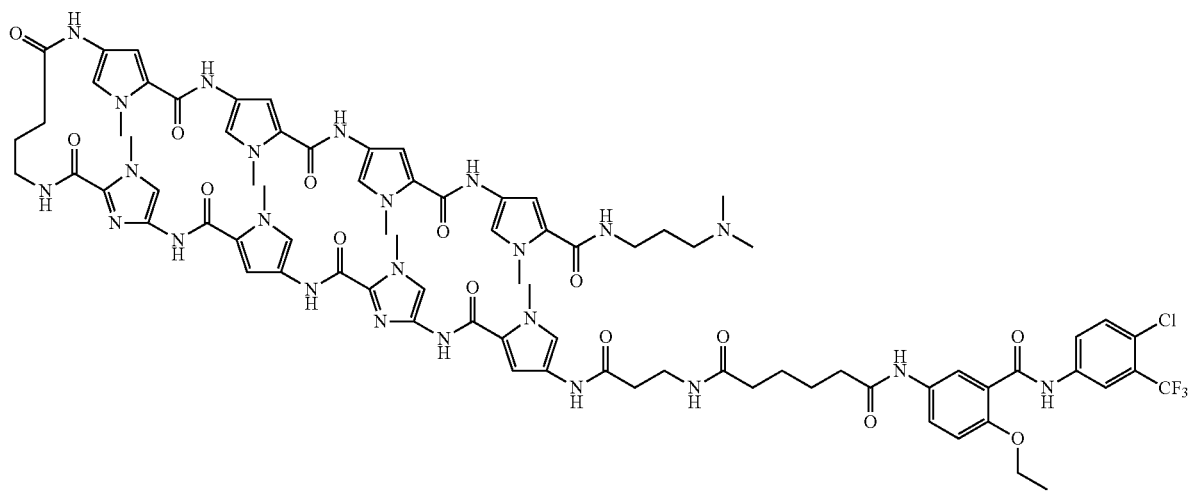
CTB-PIP-X
The conjugate of the present invention can assume the form of a pharmacologically acceptable salt. Examples thereof include: inorganic acid salts such as hydrochloride, sulfate, phosphate, and hydrobromide; and organic acid salts such as acetate, fumarate, maleate, oxalate, citrate, methanesulfonate, benzenesulfonate, and toluenesulfonate.

In the conjugate of the present invention, at least one or more moieties or molecules of the histone acetyltransferase activator, and/or the polyamide for recognizing a regulatory region of a target gene, and/or the linker moiety linking the histone acetyltransferase activator and the polyamide for recognizing a regulatory region of a target gene may be present in an enantiomer or diastereomer form or as a mixture thereof. The conjugate of the present invention encompasses a mixture of stereoisomers or each pure or substantially pure isomer. When the conjugate of the present invention is obtained in a diastereomer or enantiomer form, these diastereomers or enantiomers can be resolved by a conventional method well known in this technical field, for example, chromatography or fractional crystallization.

The conjugate of the present invention encompasses a compound labeled with a radioisotope (e.g., $^3$H, $^{13}$C, $^{14}$C, $^{15}$N, $^{18}$F, $^{32}$P, $^{35}$S, and $^{125}$I), or the like on at least one or more moieties or molecules of the histone acetyltransferase activator, and/or the polyamide for recognizing a regulatory region of a target gene, and/or the linker moiety linking the histone acetyltransferase activator and the polyamide for recognizing a regulatory region of a target gene, and a compound in which hydrogen thereon is converted to deuterium.

4. Target Gene-Specific Histone Modification-Controlling Agent

The target gene-specific histone-modifying agent of the present invention is a composition comprising the conjugate of the present invention. The target gene-specific histone modification method of the present invention is a method using the conjugate of the present invention. In this context, the phrase "target gene-specific" as used herein means being specific for one or more (in humans, the genomic region reportedly has approximately 100,000 genes, and one transcription factor as a sequence involved in gene expression reportedly recognizes specific sequences in several thousand to several hundred regions and regulates their expression; therefore, among them, for example, 1 to thousands (e.g., 1 to 5,000, 1 to 4,000, 1 to 3,000, 1 to 2,000, or 1 to 1,000), 1 to hundreds (e.g., 1 to 500, 1 to 400, 1 to 300, 1 to 200, or 1 to 100), or 1 to 50, preferably 1 to 10, more preferably 1 to 5 (5, 4, 3, 2, or 1)) targeted genes. For example, depending on a transcription factor, a 5-base recognizing sequence may regulate the expression of a group of several hundred to several thousand genes and thereby regulate biological phenomena (e.g., MYC gene has a group of 3,000 to 4,000 downstream genes). Therefore, the conjugate of the present invention, even when recognizing a sequence with low specificity (sequence common to several thousand to several hundred genes), may regulate biological phenomena and be effective for, for example, disease treatment or regenerative treatment. For the conjugate of the present invention, the number of targeted genes can be decreased, for example, by increasing the number of bases of a sequence that is recognized by the polyamide or by selecting a sequence with high specificity as the sequence that is recognized by the polyamide.

Examples of the target gene intended by the present invention include a cell control gene. Examples of the gene that is involved in cell control can include at least one gene selected from the group consisting of a tumor suppressor gene, a genetic disease suppressor gene, a gene encoding a nerve cell-controlling substance, a viral disease suppressor gene, and a gene that is involved in the maintenance and/or differentiation of stem cells or progenitor cells. At least one gene selected from the group consisting of a tumor suppressor gene, a viral disease suppressor gene, and a gene that is involved in the maintenance and/or differentiation of stem cells or progenitor cells is preferred.

The tumor suppressor gene is, for example, p16INK4a (CDKN2A) gene, p21 (CDKN1A) gene, APC gene, RASSF1 gene, RB gene, NF1 gene, NF2 gene, p19 (CDKN2D) gene, WT1 gene, VHL gene, BRCA1 gene, BRCA2 gene, CHEK2 gene, Maspin gene, p73 gene, DPC4 (SMAD4) gene, MSH2 gene, MLH1 gene, PMS2 gene, DCC gene, PTEN gene, p57KIP2 (CDKN1C) gene, PTC gene, TSC1 gene, TSC2 gene, EXT1 gene, EXT2 gene, RECK gene, or p53 gene. The tumor suppressor gene is preferably, for example, p16 gene, p21 gene, APC gene, RASSF1 gene, RB gene, RECK gene, or p53 gene.

Examples of the gene encoding a nerve cell-controlling substance include SHC3 gene, NMDA receptor genes (e.g., NR2A gene and NR2C gene), and dopamine receptor genes (e.g., DRD1 and DRD2).

Examples of the gene that is involved in the maintenance and/or differentiation of stem cells or progenitor cells include LIF (leukemia inhibitory factor) gene, OCT3/4 gene, NANOG gene, SOX2 gene, KLF4 gene, MYC gene, MYCN gene, p16INK4a (CDKN2A) gene, and MIR302C gene. The gene is preferably, for example, MYC gene, NANOG gene, OCT3/4 gene, or KLF4 gene. In an alternative preferred aspect of the present invention, the gene that is involved in the maintenance and/or differentiation of stem cells or progenitor cells is, for example, MYC gene, SOX2 gene, OCT3/4 gene, or KLF4 gene.

Examples of the viral disease suppressor gene include HIV virus suppressor genes (e.g., MX2 and TRIM 5α (Nature 502, 563-566).

When the target gene intended by the method using the conjugate of the present invention or conjugate is a tumor suppressor gene, the conjugate of the present invention or a pharmaceutical composition comprising the same, or a method using the conjugate or the pharmaceutical composition can be utilized in, for example, the prevention or treatment of cancer.

When the target gene intended by the method using the conjugate of the present invention or conjugate is a viral disease suppressor gene, the conjugate of the present invention or a pharmaceutical composition comprising the same, or a method using the conjugate or the pharmaceutical composition can be utilized in, for example, the prevention or treatment of viral disease.

When the target gene intended by the conjugate of the present invention or the method using the conjugate is a genetic disease suppressor gene, the conjugate of the present invention or a pharmaceutical composition comprising the same, or a method using the conjugate or the pharmaceutical composition can be utilized in, for example, the prevention or treatment of genetic disease.

When the target gene intended by the conjugate of the present invention or the method using the conjugate is a gene encoding a nerve cell-controlling substance, the conjugate of the present invention or a pharmaceutical composition comprising the same, or a method using the conjugate or the pharmaceutical composition can be utilized in, for example, the prevention or treatment of neurodegenerative disease.

When the target gene intended by the conjugate of the present invention or the method using the conjugate is a gene that is involved in the maintenance and/or differentiation of stem cells or progenitor cells, the conjugate of the present invention or a pharmaceutical composition comprising the same, or a method using the conjugate or the pharmaceutical composition can be utilized in, for example, the preparation of iPS cells.

5. Use

The "target gene-specific histone-modifying agent" of the present invention comprises the conjugate of the present invention, as described above. In use of the conjugate of the present invention, the conjugate may be used in combination with a carrier or an additive according to the intended purpose. Examples of such a carrier and an additive include water, acetic acid, organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arable, casein, agar, polyethylene glycol, diglycerin, glycerin, propylene glycol, Vaseline, paraffin, stearyl alcohol, stearic acid, human serum, albumin, mannitol, sorbitol, lactose, and surfactants.

The amount of the conjugate of the present invention used in the modifying agent and the modification method of the present invention can be optionally adjusted according to the intended purpose.

The present invention also includes use of the conjugate of the present invention for producing a target gene-specific histone-modifying agent. The present invention further includes use of the conjugate of the present invention for modifying histones in a target gene-specific manner.

The phrase "using the conjugate of the present invention" includes, for example, using the conjugate of the present invention in contact with cells in vitro as well as using the conjugate of the present invention by administration to a mammal (e.g., a human or a non-human mammal, for example, a rat, a rabbit, sheep, a pig, cattle, a cat, a dog, and a monkey) or a laboratory organism (e.g., except for humans; e.g., a fruit-fly, a nematode, *E. coli,* yeast, an African clawed frog, a cyprinodont, a trout, a puffer, *Arabidopsis thaliana,* and rice) or the like (using the conjugate of the present invention in vivo). The "contact" means that the conjugate of the present invention and cells are allowed to exist in the same reaction system or culture system, and includes, for example, the addition of the conjugate of the present invention to a cell culture vessel, the mixing of the cells with the conjugate of the present invention, and the culture of the cells in the presence of the conjugate of the present invention.

In a certain aspect of the present invention, it is expected that the conjugate of the present invention controls histone modification in a gene site-specific manner, and thereby allows detailed analysis of cell functions and is helpful in the elucidation of mechanisms of intractable diseases or the development of treatment methods therefor, etc. The research reagent and/or the research method of the present invention can be directed to a mammal (e.g., a non-human mammal, for example, a rat, a rabbit, sheep, a pig, cattle, a cat, a dog, and a monkey) or any of other laboratory organisms (e.g., except for humans; e.g., a fruit-fly, a nematode, *E. coli,* yeast, an African clawed frog, a cyprinodont, a trout, a puffer, *Arabidopsis thaliana,* and rice). The research reagent and/or the research method of the present invention may involve the carrier or the additive described above in the modifying agent, in addition to the conjugate of the present invention. The amount of the conjugate of the present invention used in the research reagent and/or the research method of the present invention differs depending on the intended purpose. Those skilled in the art can optionally selected, the amount of the conjugate of the present invention used according to the intended purpose.

The pharmaceutical composition of the present invention is a composition comprising the conjugate of the present invention. Various diseases can be prevented or treated by administering the pharmaceutical composition into organisms. Examples of the disease targeted by the pharmaceutical composition of the present invention include diseases involving gene mutation, for example, cancer, neurodegenerative disease or psychiatric disease, lifestyle-related disease, sleep disorder, disease and infection with strong local symptoms in the dermatological, ophthalmologic, or otolaryngologic field, allergic disease, disease involving cellular senescence, resistance to thyroid hormone, aging, cystic fibrosis, and gastrointestinal disease. Among the target diseases, examples of the cancer can include brain tumor, neck cancer, esophageal cancer, tongue cancer, lung cancer, breast cancer, pancreatic cancer, stomach cancer, cancer of the small. Intestine or the duodenum, large intestine cancer (colon cancer and rectum cancer), bladder cancer, kidney cancer, liver cancer, prostate cancer, uterus cancer, ovary cancer, thyroid gland cancer, gallbladder cancer, throat cancer, sarcoma (e.g., osteosarcoma, chondrosarcoma, Kaposi's sarcoma, myosarcoma, angiosarcoma, and fibrosarcoma), leukemia (e.g., chronic myeloid leukemia (CML), acute myeloid leukemia (AML), chronic lymphocytic leukemia (CLL), acute lymphatic leukemia (ALL), lymphoma, and multiple myeloma (MM)), childhood solid tumor (neuroblastoma, hepatoblastoma, nephroblastoma, Ewing's sarcoma, etc.), retinoblastoma, and melanoma. Examples of the lifestyle-related disease can include, but are not particularly limited to, hypertension and diabetes mellitus. Examples of the disease and infection with strong local symptoms in the dermatological, ophthalmologic, or otolaryngologic field can include psoriasis, chronic dermatitis, sinusitis, glaucoma, and retinal degeneration. Examples of the allergic disease can include atopic dermatitis and pollinosis. Examples of the disease involving cellular senescence can include skin wrinkles, sagging, and pigmentation. Examples of the neurodegenerative disease or the psychiatric disease can include mania, depression, schizophrenia, autism, bipolar disorder, Alzheimer's disease, sleep disorder, and dementia.

The cancer can be prevented or treated by using the conjugate of the present invention to activate histone acetylation and to promote the expression of a tumor suppressor gene (e.g., p16 gene, p21 gene, APC1 gene, RASSF1 gene, RB gene, or p53 gene).

The viral disease (e.g., AIDS) can be prevented or treated by using the conjugate of the present invention to activate histone acetylation and to promote the expression of a HIV virus suppressor gene (e.g., MX2 and TRIM 5α).

The genetic disease can be prevented or treated by using the conjugate of the present invention to activate histone acetylation and to promote the expression of a genetic disease suppressor gene.

The neurodegenerative disease can be prevented or treated by using the conjugate of the present invention to activate histone acetylation and to promote the expression of GDNP or neurturin gene or to silence AFP (amyloid precursor protein) gene.

The cystic fibrosis or the gastrointestinal disease can be prevented or treated by using the conjugate of the present invention to activate histone acetylation and to promote the expression of CFTR gene or to silence this gene.

The pharmaceutical composition of the present invention may be in any of dosage forms of oral administration and parenteral administration. These dosage forms can be formulated according to a routine method and may contain a pharmaceutically acceptable carrier or additive. Examples of such a carrier and an additive include water, acetic acid, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arable, casein, agar, polyethylene glycol, diglycerin, glycerin, propylene glycol, Vaseline, paraffin, stearyl alcohol, stearic acid, human serum albumin, mannitol, sorbitol, lactose, and surfactants acceptable as pharmaceutical additives.

The additive is selected alone or in appropriate combination from those described above depending on the dosage form of the pharmaceutical composition of the present invention. Examples of the dosage form for oral administration include tablets, capsules, fine granules, powders, granules, solutions, syrups, sprays, endermic liniments, eye drops, and preparations for external use. Alternatively, the oral administration may be performed in an appropriate dosage form. Examples of the dosage form for parenteral administration include injections. The injections can be administered systemically or locally by, for example, intravenous injection (e.g., drip infusion), subcutaneous injection, or intratumoral injection.

For example, for use as a preparation for injection, the pharmaceutical composition of the present invention is dissolved in a solvent (e.g., saline, a buffer solution, a glucose solution, and 0.1% acetic acid), and this solution can be supplemented with an appropriate additive (human serum albumin, PEG, a mannose-modified dendrimer, a cyclodextrin conjugate, etc.) and used. Alternatively, the pharmaceutical composition of the present invention may be freeze-dried for a dosage form that is dissolved before use. For example, a sugar alcohol or a saccharide, such as mannitol or glucose, can be used as an excipient for freeze drying.

The dose of the pharmaceutical composition of the present invention or the conjugate of the present invention differs depending on age, sex, symptoms, administration route, the number of doses, and the dosage form. The dose, for example, for an adult human (60 kg) is 0.01 to 1,000 mg, preferably 0.1 to 100 mg, more preferably 1 to 30 mg, per day. The administration method is appropriately selected according to the age of a patient and symptoms. The daily dose, for example, may be administered in one portion or in two to four divided portions.

The pharmaceutical composition and/or the prevention, treatment, or diagnosis method of the present invention can be directed to every organism, particularly, mammal (e.g., human, rat, rabbit, sheep, pig, cattle, cat, dog, and monkey), which exploits double-stranded DNA in biocontrol.

The present invention also includes a kit comprising the conjugate of the present invention. The kit may contain, in addition to the conjugate of the present invention, the pharmaceutically acceptable carrier or additive described above, reagents, auxiliary agents, a dedicated container, other necessary accessories, an instruction manual, etc. The kit of the present invention may be used as a kit for target gene-specific modification control, or for the prevention, treatment, or diagnosis of cancer or for research reagents.

6. Production Method

An exemplary method for producing the conjugate of the present invention is shown below, though the method for producing the conjugate of the present invention is not limited thereto. Examples of the production method include a production method by liquid-phase reaction and a production method by a solid-phase reaction.

(Production Method by Liquid-Phase Reaction)

A typical production scheme for CTB-PIP-I is shown below. In this production method, for example, the synthesis of the CTB moiety is carried out according to a method described in J. Phys. Chem., B 2007, 111, 4527-4534, and the solid-phase synthesis of the PIP moiety is carried out according to a method described in Sci. Rep., 2012, 2, 544 and Sci. Rep., 2014, 4, 3843.

[Chem. 24]

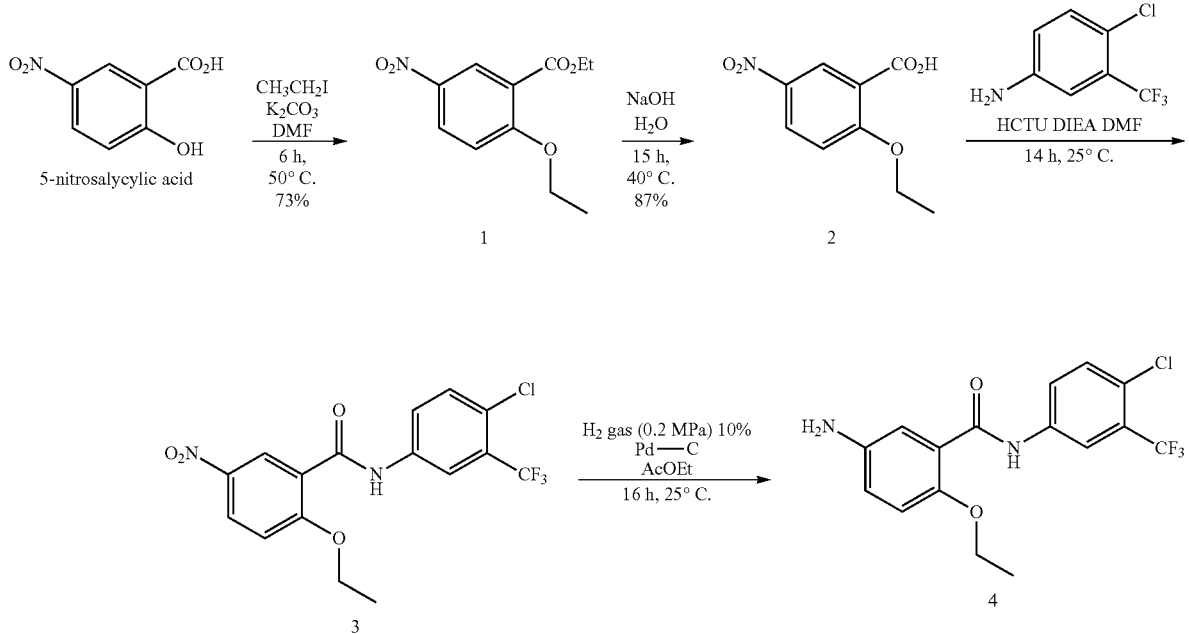

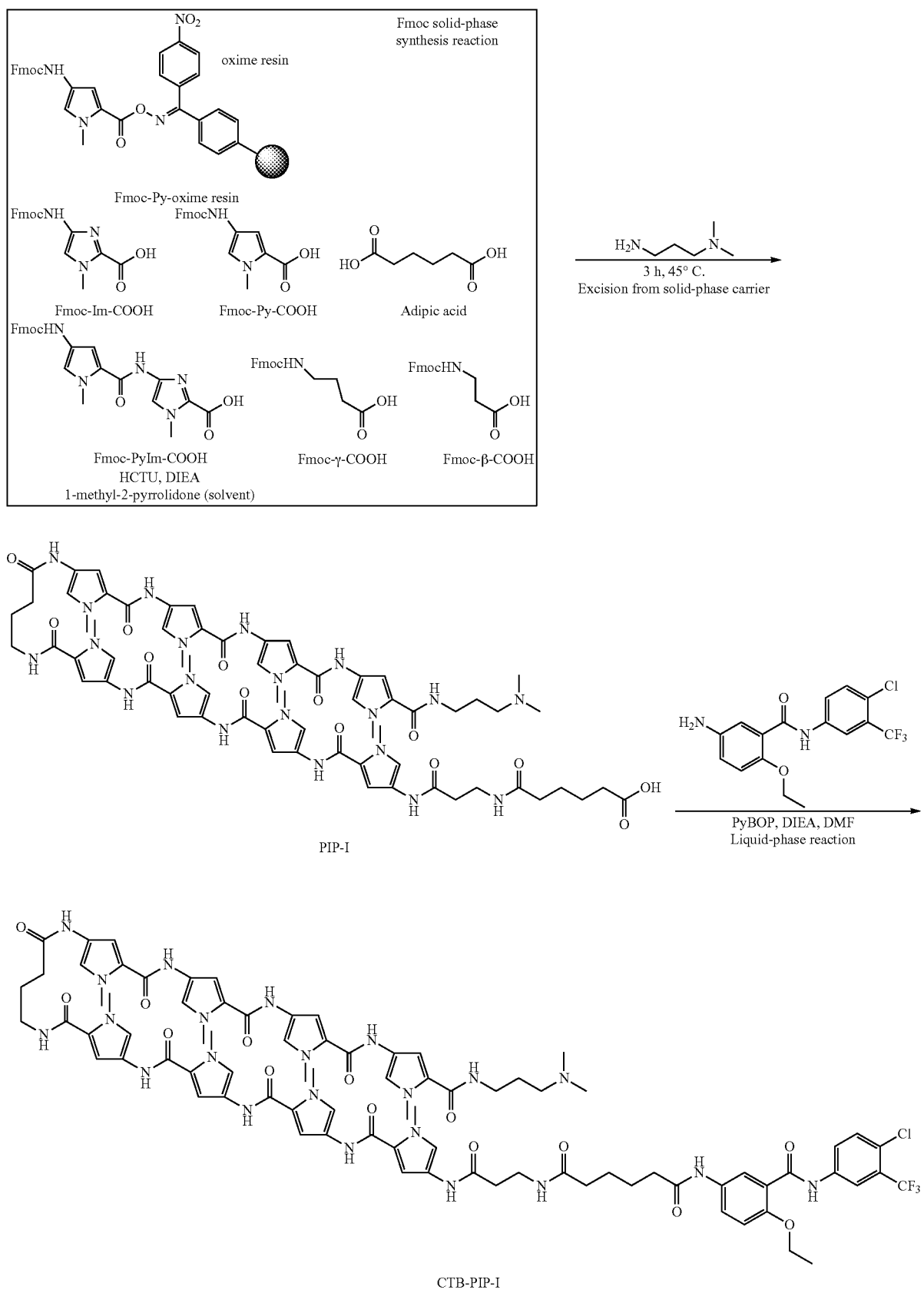

The production procedures are conducted according to the following steps:

1. A derivative (e.g., an amino derivative) of a benzamide compound represented by the formula (I)' which is a HAT activator is prepared.

[Chem. 26]

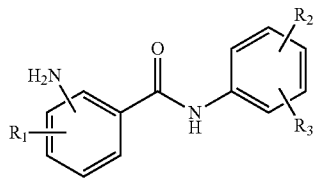
(I)'

2. (a) PIP of interest is optionally prepared depending on the sequence specificity of a target.

(b) The formula L1':

[Chem. 27]

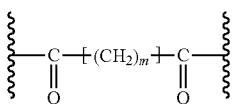

is optionally introduced into a solid-phase synthesis step according to the need to prepare a linker moiety.

3. The benzamide derivative (formula (I)') prepared in step 1 as a CTB synthesis unit and the carboxylic acid moiety-containing PIP prepared in step 2 are linked through condensation reaction under liquid-phase conditions to produce the desired CTB-PIP conjugate.

(Production Method by Solid-Phase Reaction)

A typical production scheme for CTB-PIP-I is shown below. This production method is a novel production method found by the present inventors.

[Chem. 28]

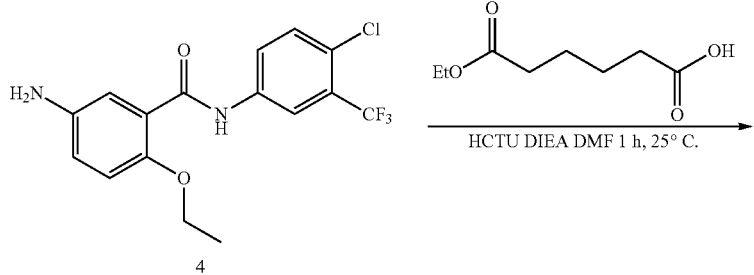

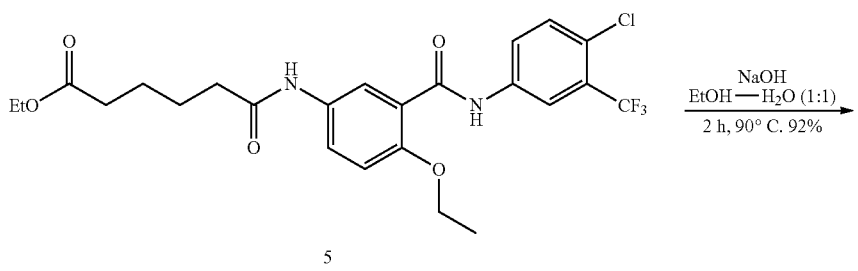

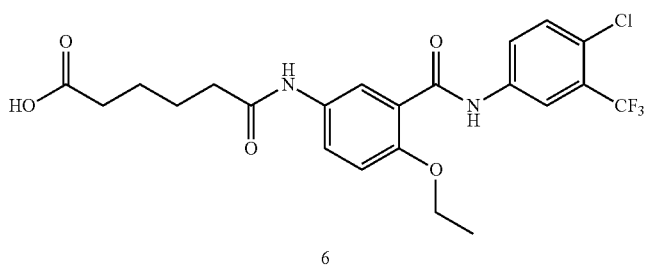

[Chem. 29]

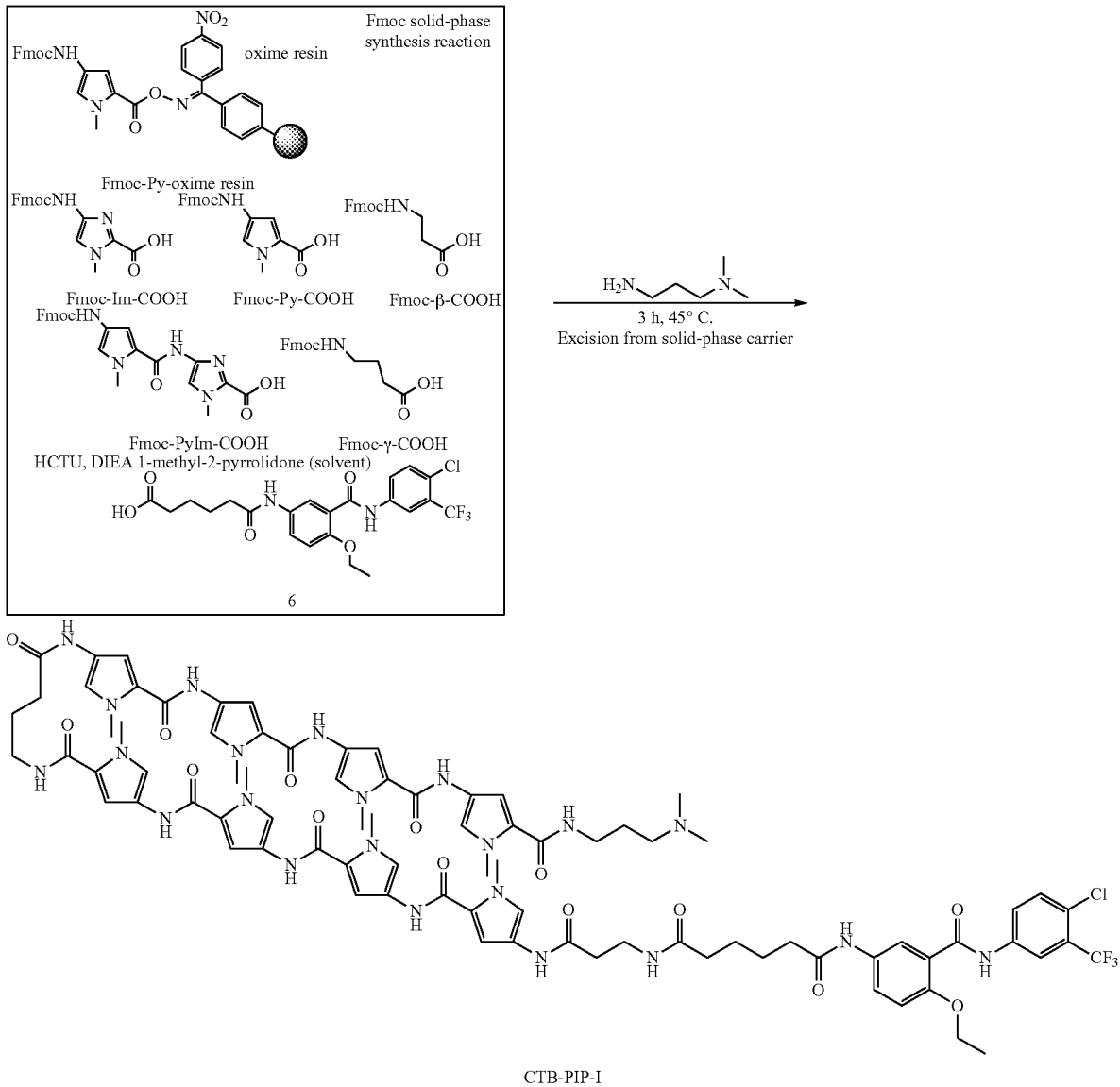

CTB-PIP-I

The production procedures are conducted according to the following steps:

1. (a) A carboxylic acid moiety-containing CTB derivative (e.g., compound 6) of a benzamide compound represented by the formula (I)' which is a HAT activator is prepared in the same way as in the production method by liquid-phase reaction.

(b) optionally, as needed, a monoalkyl ester compound of an alkenyldicarboxylic acid represented by the formula (III):

[Chem. 30]

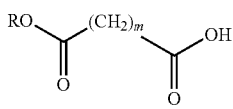

(III)

wherein R is a protective group for the carboxyl group, and m is any integer of 1 to 6 as a partial structure of a linker
is reacted with the obtained CTB derivative to bind the compound represented by the formula (III) to the derivative of the formula (I)', followed by performing hydrolysis reaction of the resulting product to produce a compound (IV) represented by the formula (IV):

[Chem. 31]

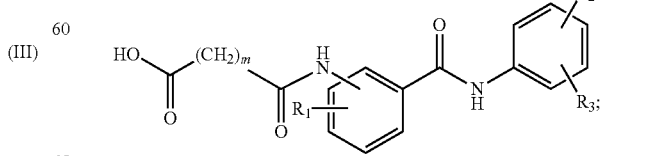

(IV)

2. The obtained compound (IV) is introduced into the solid-phase synthesis of PIP or a modified form thereof, followed by excision from the solid-phase carrier using a reagent to obtain the desired CTB-PIP conjugate (e.g., CIS-PIP-I); and 3. optionally, the CTB-PIP conjugate is purified.

The term "protective group for the carboxyl group" is most preferably an ester group that is removable by hydrolysis reaction. Examples of the R group include an alkyl group having 1 to 3 carbon atoms and specifically include methyl, ethyl, isopropyl, and t-butyl.

The PIP or the modified form thereof includes a compound having a structural formula represented by the abbreviation A, G, I, K, L, or X described above. In the conjugate of the present invention, the carboxylic acid of the linker moiety derived from the formula (III) in the formula (IV) is bonded to the amino group of PIP to produce the desired CTB derivative.

The production method by solid-phase reaction described above has many advantages as compared with the production method by liquid-phase reaction.

In the production method by liquid-phase reaction, the synthetic intermediate PIP having a carboxylic acid moiety needs to be purified in order to remove dimethylaminopropylamine used in the excision. This requires time and effort and also decreases yields due to the purification. In addition, disadvantageously, the CTB-PIP conjugate needs to be purified even after the final condensation step carried out by liquid-phase reaction. Use of the production method by solid-phase reaction can solve all of these problems.

The disadvantage of the production method by solid-phase reaction includes, because of using a CTB derivative having a carboxylic acid moiety in the step of solid-phase reaction, a larger amount necessary for synthesis than that in the production method by liquid-phase reaction. However, this does not impair the advantages of the production method by solid-phase reaction.

As a result, a conjugate of the benzamide derivative of the formula (I) having various substituents and PIP can be easily produced through the use of the production method by solid-phase reaction.

EXAMPLES

Hereinafter, the present invention is described further specifically with reference to Examples. However, the present invention is not intended to be limited by these Examples.

Example 1

Method for Producing CTB Derivative 4 for Use in Liquid-Phase Synthesis (1) Synthesis of Compound 1

[Chem. 32]

To a solution of 5-nitrosalicylic acid (1.00 g, 5.46 mmol) dissolved in 15 mL of DMF, $K_2CO_3$ (4.52 g, 32.8 mmol) and iodoethane (2.2 mL, 27.5 mol) were added, and the mixture was stirred at 50° C. for 6 hours. The solvent was distilled off, and the resulting yellow residue was washed with water (20 mL) to obtain compound 1 (955 mg, 3.99 mmol, 73%) as a yellow powder.

1: $^1$H NMR (600 MHz, CDCl$_3$) δ 8.67 (d, J=2.7 Hz, 1H; Ar—H), 8.33 (dd, J=2.7, 9.6 Hz, 1H; Ar—H), 7.02 (d, J=9.6 Hz, 1H; Ar—H), 4.39 (q, J=7.3 Hz, 2H; CH$_2$), 4.23 (q, J=7.3 Hz, 2H; CH$_2$), 1.52 (t, J=7.3 Hz, 3H; CH$_3$), 1.41 (t, J=7.3 Hz, 3H; CH$_3$)

(2) Synthesis of Compound 2

[Chem. 33]

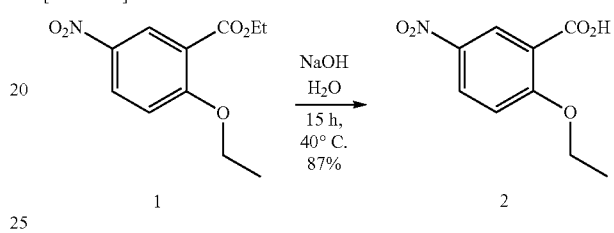

To a solution of compound 1 (950 mg, 3.99 mmol) dissolved in water (15 mL), NaOH (1.0 g, 25 mmol) was added, and the mixture was stirred at 40° C. for 15 hours. A white precipitate obtained by neutralization with dilute hydrochloric acid was filtered and washed with water (10 mL) to obtain compound 2 (733 mg, 3.47 mmol, 87%) as a white powder.

1: $^1$H NMR (600 MHz, CDCl$_3$) δ 9.06 (d, J=2.8 Hz, 1H; Ar—H), 8.44 (dd, J=2.8, 8.9 Hz, 1H; Ar—H), 7.16 (d, J=8.9 Hz, 1H; Ar—H), 4.45 (q, J=6.9 Hz, 2H; CH$_2$), 1.64 (t, J=6.9 Hz, 3H; CH$_3$)

(3) Synthesis of Compound 3

[Chem. 34]

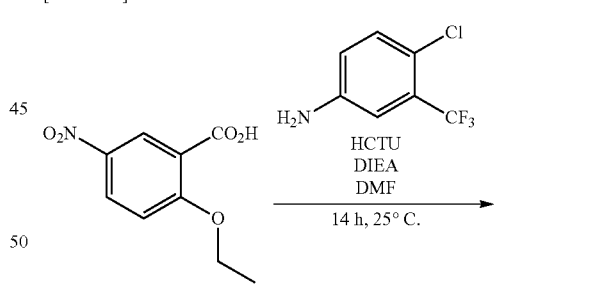

To a solution of compound 2 (733 mg, 3.47 mmol) dissolved in DMF (11 mL), HCTU (1.58 g, 3.82 mmol) and N,N-diisopropylethylamine (0.73 mL, 4.16 mmol) were added, and the mixture was stirred for 10 minutes. Then, 5-amino-2-chlorobenzotrifluoride (680 mg, 3.47 mmol) was further added thereto, and the mixture was stirred at 25° C. for 14 hours. The solvent was distilled off, and a product 3 (1.85 g, containing HCTU) was obtained as a brown powder from the resulting yellow residua using 5% hydrochloric acid (20 mL) and water (20 mL).

3: ESI-TOF-MS (positive) m/z calcd for $C_{16}H_{13}ClF_3N_2O_4{}^+$ [M+H]$^+$ 389.0516; found 389.0527.

(4) Synthesis of Compound 4

[Chem. 35]

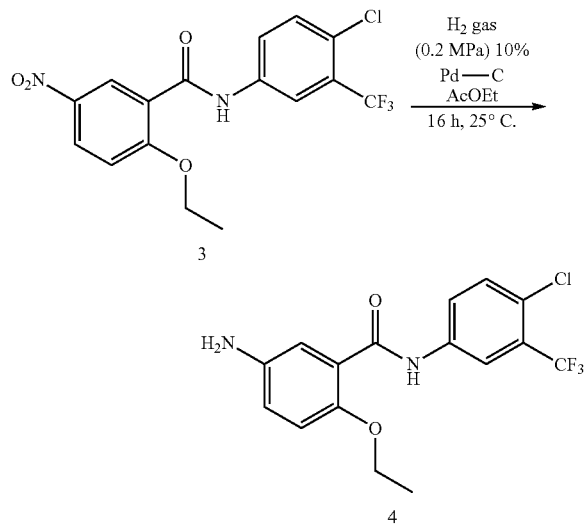

To a solution of compound 3 (500 mg, containing HCTU) dissolved in ethyl acetate (10 mL), 10% Pd—C (20 mg) was added, and the mixture was stirred at room temperature for 16 hours under hydrogen gas (0.2 MPa). After celite filtration using a $CH_2Cl_2$-MeOH solution, the solvent was distilled off, and the resulting residue was purified by silica gel column chromatography to obtain yellow powder 4 (387 mg, 1.08 mmol).

4: $^1$H NMR (600 MHz, CDCl$_3$): δ 10.45 (s, 1H; NH), 7.99 (d, 1H; CH), 7.85 (d, 1H; CH), 7.60 (d, 1H; CH), 7.46 (d, 1H; CH), 6.87 (d, 1H; CH), 6.63 (dd, 1H; CH), 4.25 (q, 2H; CH$_2$), 3.60 (br, 2H; NH$_2$), 1.59 (t, 3H; CH$_3$). ESI-TOF-MS (positive) m/z calcd for $C_{16}H_{15}ClF_3N_2O_2{}^+$ [M+H]$^+$ 359.0815; found 359.0774.

Example 2

Method for Producing CTB Derivative 6 for Use in Solid-Phase Synthesis
(1) Synthesis of Compound 5

[Chem. 36]

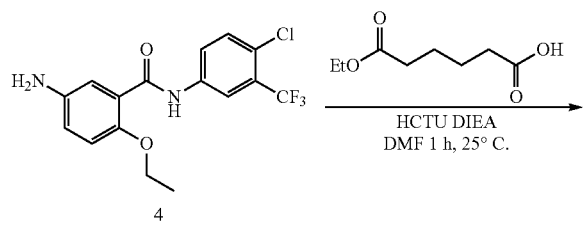

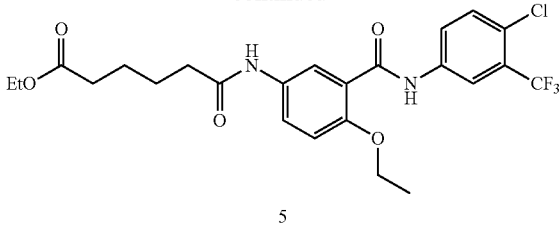

To a solution of compound 4 (660 mg, containing HCTU) dissolved in DMF (7 ml), HCTU (820 mg, 1.98 mmol) and N,N-diisopropylethylamine (0.41 mL, 2.38 mmol) were added, and the mixture was stirred at 25° C. for 1 hour. The solvent was distilled off, and 1 N NaOH (20 mL) for HCTU removal was added to the resulting brown residue. The mixture was filtered to obtain crude product 5 (580 mg, 1.13 mmol) as a light brown powder.

5: ESI-TOF-MS (positive) m/z calcd for $C_{24}H_{27}ClF_3N_2O_5{}^+$ [M+H]$^+$ 515.1561; found 515.1127.

(1) Synthesis of Compound 6

[Chem. 37]

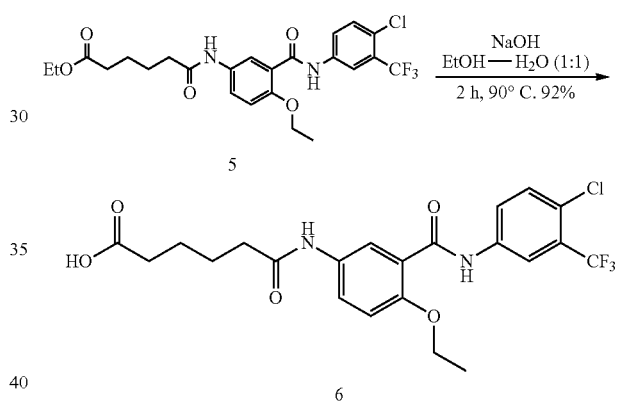

To a solution of compound 5 (580 mg, 1.13 mmol) dissolved in water (20 mL) and EtOH (20 mL), NaOH (1.0 g, 25 mmol) was added, and the mixture was stirred at 90° C. for 2 hours to prepare a brown solution. A white precipitate was obtained by EtOH removal and neutralization with dilute hydrochloric acid, collected by filtration, and washed with water (10 mL) to obtain compound 6 (503 mg, 1.04 mmol, 92%) as a white powder.

6: $^1$H NMR (600 MHz, d$_6$-DMSO) δ 10.51 (s 1H; NH), 9.92 (s, 1H; NH), 8.33 (s, 1H; Ar—H), 7.95 (d, J=8.9 Hz, 1H; Ar—H), 7.87 (d, J=2.0 Hz, 1H; Ar—H), 7.72 (m, 2H; Ar—H×2), 7.13 (d, J=8.9 Hz, 1H; Ar—H), 4.13 (q, J=6.9 Hz, 2H; CH$_2$), 2.29 (t, J=7.3 Hz, 2H; CH$_2$), 2.24 (t, J=7.3 Hz, 2H; CH$_2$), 1.59 (m, 2H; CH$_2$), 1.52 (m, 2H; CH$_2$), 1.36 (t, J=6.9 Hz, 3H; CH$_3$). ESI-TOF-MS (positive) m/z calcd for $C_{22}H_{23}ClF_3N_2O_5{}^+$ [M+H]$^+$ 487.1168; found 487.1248.

Example 3

Method for Producing CTB-PIP-I
(1) Method for Producing CTB-PIP-I Using Compound 4 in Liquid-Phase Reaction
Synthesis of PIP by Fmoc Solid-Phase Synthesis Method:
PSSM-8 peptide synthesis apparatus (Shimadzu Corp., Kyoto, Japan) was used in solid-phase synthesis. PIP was synthesized by the Fmoc solid-phase synthesis method from 43 mg of Pmoc-Py-oxime resin (approximately 0.42 mmol/g, 100-200 mesh). The reaction cycle is as follows: deprotection was performed twice (4 minutes each) using a DMF solution of 20% piperidine. Coupling was performed for 60 minutes using carboxylic acid, HCTU (88 mg), N,N-diisopropylethylamine (DIEA) (36 µL), and 1-methyl-2-pyrrolidone (NMP). Washing was performed five times (1 minute each) using DMF. Each coupling reagent per step was prepared as a NMP solution in the following amount: Fmoc-Py-COOH (77 mg), Fmoc-Im-COOH (77 mg), Fmoc-PyIm-COOH (70 mg), Fmoc-β-COOH (66 mg), Fmoc-γ-COOH (69 mg), and adipic acid (31 mg). All condensation steps were performed by single coupling, and stirring was performed by the bubbling of nitrogen gas. As a typical example, 40 mg of a resin and 1 mL of NMP were placed in a 2.5-mL plastic reaction vessel and left for 30 minutes to swell the resin. Fmoc monomers, HCTU, and 1 mL of NMP were added to a 2-ml plastic centrifugal tube and placed at positions according to a sequence. All lines were washed with NMP after solution transfer. After the completion of synthesis, the resin was washed with a 0.1 N NaOH solution, washed with water, then washed twice with 1 mL of DMF and twice with 1 mL of methanol, and dried under reduced pressure at room temperature in a desiccator.

Excision and Purification:

To the dried sample resin, 0.5 mL of 3-(dimethylamino)-1-propylamine was added, and the resin was treated at 45° C. for 3 hours for excision. The resin was removed by filtration, and the filtrate was powdered using $CH_2Cl_2$-$Et_2O$ to obtain 33 mg of a yellow unpurified powder of Py-Im polyamide. The powder was purified by flash column chromatography (eluting solution: 0.1% aqueous TFA solution and acetonitrile with a linear gradient of 0 to 45% (0 to 45 min), flow rate: 18 mL/min, detection: 254 nm) to obtain PIP-I (10 mg) as a white powder.

Condensation Reaction in Liquid Phase and Purification:

To the reaction container of the purified PIP-I (2.0 mg), CTB derivative 4 (1.6 mg), PyBOP (5.0 mg), and diisopropylethylamine (DIEA) (2.0 µL) were added, dissolved in DMF (100 µL), and stirred at room temperature for 8 hours in a nitrogen atmosphere. After the completion of condensation reaction, the solvent was distilled off, and the resulting residue was purified by reverse-phase HPLC (eluting solution: 0.1% aqueous TFA solution and acetonitrile with a linear gradient of 0 to 50% (0 to 40 min), detection: 254 nm). The compound of interest was freeze-dried to obtain CTB-PIP-I (0.4 mg) as a white powder. ESI-TOF-MS (positive) m/z calcd for $C_{80}H_{93}$ $ClF_3N_{24}O_{14}{}^{2+}$ $[M+2H]^{2+}$ 853.3511; found 853.3577.

(2) Method for Producing CTB-PIP-I Using Compound 6 in Solid-Phase Synthesis Reaction Synthesis of PIP by Fmoc Solid-Phase Synthesis Method:

Solid-phase synthesis was carried out under the same conditions as in the paragraph (1). Each coupling reagent was prepared as a NMP solution in the following amount: Fmoc-Py-COOH (77 mg), Pmoc-Im-COOH (77 mg), Fmoc-PyIm-COOH (70 mg), Fmoc-β-COOH (66 mg), Fmoc-γ-COOH (69 mg), and CTB derivative 6 (103 mg). After the completion of synthesis, the resin was washed twice with 1 mL of DMF and twice with 1 mL of methanol and dried under reduced pressure at room temperature in a desiccator.

Excision and Purification:

To the dried sample resin, 0.5 mL of 3-(dimethylamino)-1-propylamine was added, and the resin was treated at 45° C. for 3 hours for excision. The resin was removed by filtration, and the filtrate was powdered using $CH_2Cl_2$-$Et_2O$ to obtain 38 mg of a yellow unpurified powder of PIP. The powder was purified by flash column chromatography (eluting solution: 0.1% aqueous TFA solution and acetonitrile with a linear gradient of 0 to 45% (0 to 45 min), flow rate: 18 mL/min, detection: 254 nm) to obtain CTB-PIP-I of interest (13 mg) as a white powder. ESI-TOF-MS (positive) m/z calcd for $C_{80}H_{93}$ $ClF_3N_{24}O_{14}{}^{2+}$ $[M+2H]^{2+}$ 853.3511; found 853.3577.

The production method using compound 6 in solid-phase synthesis reaction was also applied to the synthesis of various conjugates CTB-PIP-A, -G, -K, -L, and -X. Efficient synthesis was confirmed to be feasible.

Example 4

Gene Clustering Analysis

Cell Culture and Optimization of Treatment Condition:

Human dermal fibroblasts (HDFs) of a 54-year-old Caucasian woman were purchased from Cell Applications, Inc. The cells cryopreserved at P4 were thawed and then used in a screening experiment up to the 4th passage. The cells were cultured in a Dulbecco's modified eagle medium (DMEM, Nacalai Tesque, Inc., Japan) containing 10% fetal bovine serum (FBS, Japan Serum) (Pandian, G. N. et al., Sci. Rep. 2014, 4, e3843). HDFs of P6 were treated with trypsin at 37° C. for 5 minutes and cultured at 37° C. for 48 hours with an effector (CTB, SAHA, CTB-PIP-I, or SAHA-PIP-I) at a final concentration of 1 µM and 0.5% DMSO in the presence of 5% $CO_2$ (Pandian, G. N. et al., ACS Chem. Biol. 20 14, 10.1021/cb500724t). Cells treated with 0.5% DMSO were used as a control. In a CTB-PIP-I concentration optimization experiment, the concentration of CTB-PIP-I was changed to 500 nM, 1 µM, 5 µM, and 10 µM. The concentrations larger than 1 µM had no significant influence on induction patterns. In study to optimize a treatment time, conditions of 24 hours, 48 hours, and 72 hours were tested. At the time point 48 hours, consistent expression was able to be confirmed, suggesting that this time point is optimal. Accordingly, treatment with 1 µM of the effector for 48 hours was used in all experiments.

Figure 3A:
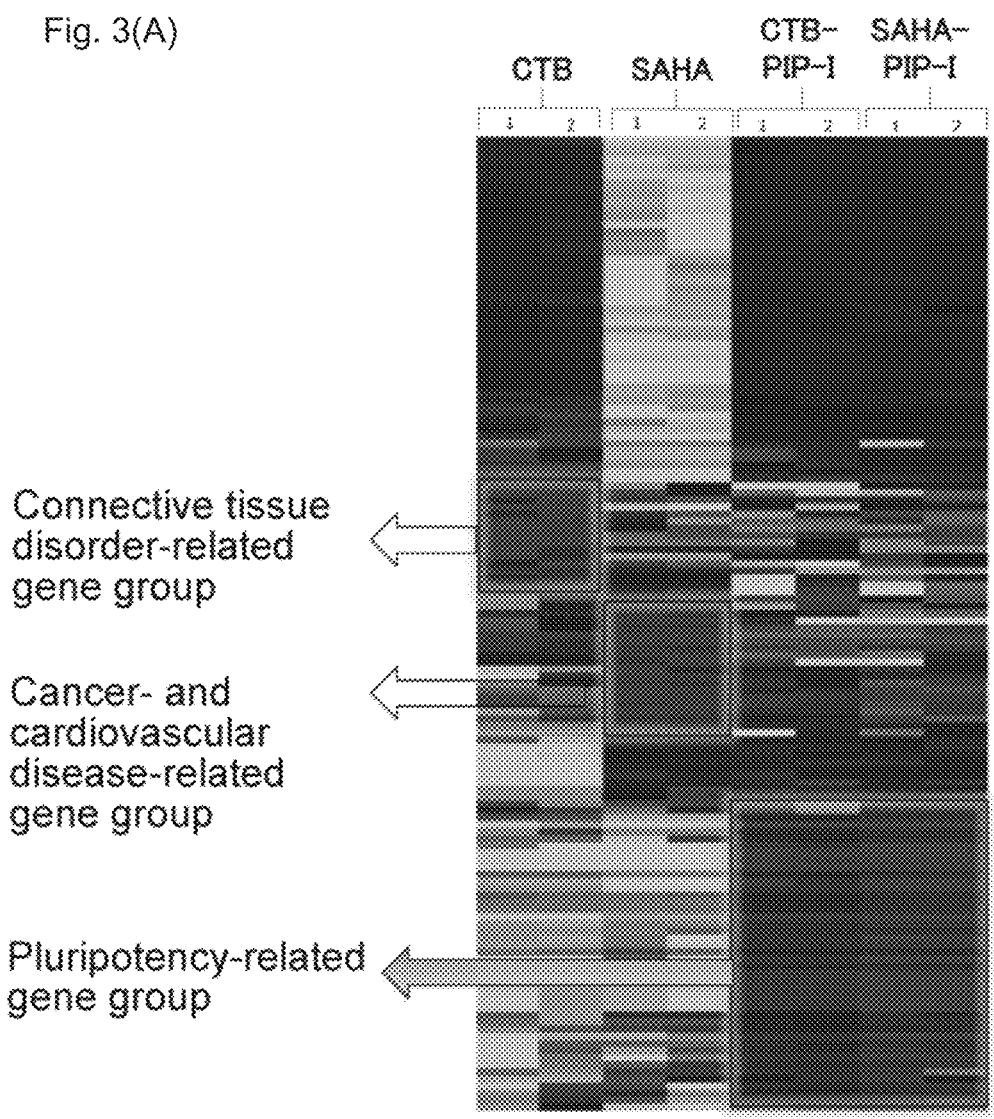
FIG. 3A is a drawing showing results of microarray-analyzing influence on genome-wide gene expression using CTB, SAHA, CTB-PIP-I, and SAHA-PIP-I.

Microarray Analysis:

HDFs were treated with 1 µM of the effector. After 48 hours, total RNA was isolated therefrom using RNeasy MINI Kit (Qiagen N.V., CA, USA) according to the manual. A microarray experiment was conducted using Human Gene 2.1 ST Array (Affymetrix, Inc., USA) (Pandian, G. N. et al., ACS Chem. Biol. 2014, 10.1021/cb500724t). Sample information associated with raw data was processed with Expression Console (Affymetrix, Inc., USA) and Transcriptome Analysis Console (Affymetrix, Inc., USA) (FIG. 3A). The microarray data was interpreted by Ingenuity pathway analysis (Pandian, G. N. et al., Sci. Rep. 2014, 4, e3843; and Pandian, G. N. et al., ACS Chem. Biol. 2014, 10.1021/cb500724t). Cluster 3.0 was used in cluster analysis without any objective variable, and the analysis results were visualized using Java™ Treeview (Pandian, G. N. et al., ACS Chem. Biol. 2014, 10.1021/cb500724t). The association of the obtained data with genes contained in canonical pathways or libraries in the Ingenuity Pathway Knowledge Base was evaluated by calculating p values by Fisher's exact test. As for scatter diagram analysis, transcripts whose expression was elevated in HDFs treated with CTB-PIP-I (>2-fold, p<0.05 as compared with cells treated with DMSO) were extracted and plotted against data obtained in HDFs treated with SAHA-PIP-I (FIG. 3B).

Figure 3B:
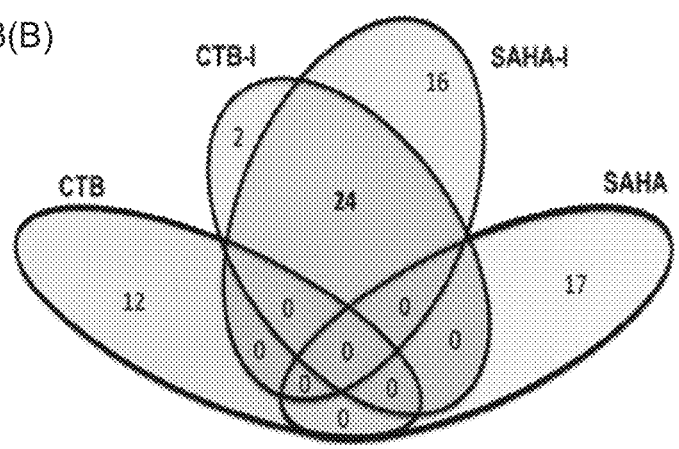
FIG. 3B is a drawing showing results of clustering analysis.

The analysis results are shown in FIG. 3B. FIG. 3B shows results of clustering-analyzing influence on genome-wide gene expression using CTB, SAHA, CTB-PIP-I, and SAHA-PIP-I. This microarray analysis revealed that CTB activates the expression of a connective tissue disorder-related gene group, and SAHA activates the expression of cancer- and cardiovascular disease-related gene groups. By contrast, CTB-PIP-I and SAHA-PIP-I were found to activate the expression of similar pluripotency-related gene groups. The important point is that the specificity of the binding of PIP to DNA influenced genes to be elevated. As shown in FIG. 3B, any gene common among 3 groups of SAHA, CTB, CTB-PIP, and SAHA-PIP was not observed in gene groups activated 5-fold or more. These microarray results also suggest the possibility that CTB or SAHA (columns of FIG. 3A) can activate the expression of a totally different gene group (rows of FIG. 3A) by conjugation with PIP.

Example 5

Induction of Expression of Pluripotency Gene Quantification of Gene Expression:

Each gene expression level was quantified using ReverTra Ace qPCR kit (Toyobo Co., Ltd., Japan). Quantitative reverse-transcript ion PCR was performed in triplicate using THUNDERBIRD SYBR qPCR Mix (Toyobo Co., Ltd., Japan), followed by analysis using ABI 7300 Real-Time PCR System (Applied Biosystems, Inc., USA) (Han, L. et al., Angew. Chem. Int. Ed. 2013, 52, 13410; Pandian, G. N. et al., Sci. Rep. 2014, 4, e3843; and Pandian, G. N. et al., ACS Chem. Biol. 2014, 10.1021/cbS00724t). Relative expression levels to cells treated with DMSO were calculated with GAPDH as internal standards. Primer pairs used in the reverse-transcription PCR are as described in Pandian, G. N. et al., ACS Chem. Biol. 2014, 10.1021/eb500724t and are shown below.

```
Sequence of LIN28B forward primer:
                                        (SEQ ID NO: 1)
5'-TGATAAACCGAGAGGGAAGC-3', sequence of LIN28B reverse primer:
                                        (SEQ ID NO: 2)
5'-TGTGAATTCCACTGGTTCTCC-3';

Sequence of OCT3/4 forward primer:
                                        (SEQ ID NO: 3)
5'-AGCCCTCATTTCACCAGGCC-3', sequence of OCT3/4 reverse primer:
                                        (SEQ ID NO: 4)
5'-TGGGACTCCTCCGGGTTTTGC-3';

Sequence of SOX2 forward primer:
                                        (SEQ ID NO: 5)
5'-GGGAAATGGGAGGGGTGCAAAAGAGG-3', sequence of SOX2 reverse primer:
                                        (SEQ ID NO: 6)
5'-TTGCGTGAGTGTGGATGGGATTGGTG-3';

Sequence of DPPA4 forward primer:
                                        (SEQ ID NO: 7)
5'-ATTCCACTGCTCTCCTTGAG-3', sequence of DPPA4 reverse primer:
                                        (SEQ ID NO: 8)
5'-GTGAACCCAACCATCTGTGT-3';

Sequence of EPCAM forward primer:
                                        (SEQ ID NO: 9)
5'-GGTGAGATGCATAGGGAACT-3', sequence of EPCAM reverse primer:
                                        (SEQ ID NO: 10)
5'-AAGCCAGTTTCAAGCTGC-3';

Sequence of NANOG forward primer:
                                        (SEQ ID NO: 11)
5'-AATACCTCAGCCTCCAGCAGATG-3',
```

```
-continued
sequence of NANOG reverse primer:
                                        (SEQ ID NO: 12)
5'-TGCGTCACACCATTGCTATTCTTC-3';

Sequence of ZIC3 forward primer:
                                        (SEQ ID NO: 13)
5'-CTAGCTACTTGCTGTTTCCC-3', sequence of ZIC3 reverse primer:
                                        (SEQ ID NO: 14)
5'-CCACGTTCACTCCCATGTT-3';

Sequence of SALL4 forward primer:
                                        (SEQ ID NO: 15)
5'-TGAACCACCCAGGGAATGA-3', sequence of SALL4 reverse primer:
                                        (SEQ ID NO: 16)
5'-GAAGTCTTCTGAAGGCACAG-3';

Sequence of MIR302C forward primer:
                                        (SEQ ID NO: 17)
5'-GGGTACCTGCTGTGTGAAACAA-3', sequence of MIR302C reverse primer:
                                        (SEQ ID NO: 18)
5'-CCTCCACTGAAACATGGAAGCA-3';
and Sequence of GAPDH forward primer:
                                        (SEQ ID NO: 19)
5'-ACCACAGTCCATGCCATCAC-3', sequence of GAPDH reverse primer:
                                        (SEQ ID NO: 20)
5'-TCCACCACCCTGTTGCTGTA-3'.
```

Statistical significance was determined by t test.

Figure 4:
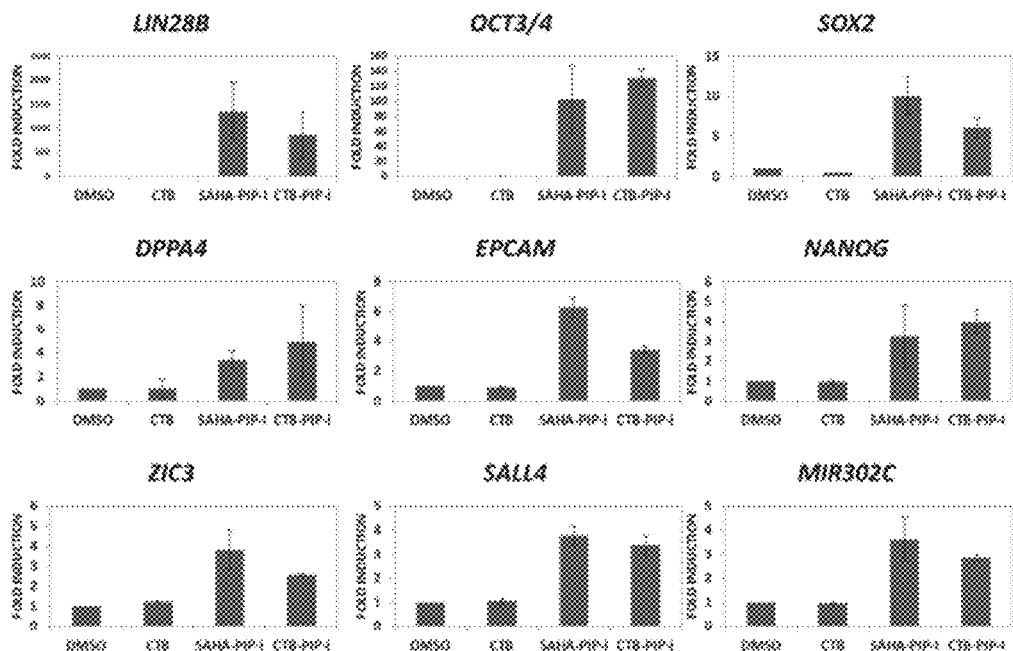
FIG. 4 is a drawing showing results of comparing SAHA-PIP-I and CTB-PIP-I by qRT-PCR analysis as to the induction of the expression of 9 pluripotency-related genes. In the drawing, rises in the expression of the target genes by SAHA-PIP-I and CTB-PIP-I were compared with DMSO and CTB as references for comparison.

The results are shown in FIG. 4. FIG. 4 shows results of qRT-PCR analysis as to the induction of the expression of 9 pluripotency-related genes, wherein rises in the expression of the target genes by SAHA-PIP-I and CTB-PIP-I were compared with DMSO and CTB as references for comparison. The 9 pluripotency-related gene groups are as follows: LIN28B gene, OCT-3/4 gene, SOX2 gene, DPPA4 gene, EPCAM gene, NANOG gene, ZIC3 gene, SALL4 gene, and MIR302C gene. These results indicated that unlike CTB, CTB-PIP-I elevated the expression of the pluripotency-related gene group. This also suggests that, as in the microarray results of FIGS. 3A and 3B, the selectivity of genes to be activated is derived from the specificity of the binding of the PIP moiety in the SAHA-PIP-I and CTB-PIP-I structures to DNA. This also suggests that, as in the microarray results of FIGS. 3A and 3B, the selectivity of genes to be activated is derived from the specificity of the binding of the PIP moiety in the SAHA-PIP-I and CTB-PIP-I structures to DNA.

Example 6

HDAC Inhibitory Activity Evaluation

Trichostatin A (TSA), SAHA, and CTB were evaluated for their inhibitory activity against Color de Lys™ Substrate Deacetylation using nucleus extracts of HeLa cells. The nucleus extracts of HeLa cells were incubated with 0.2 mM of a substrate at 37° C. After 30 minutes, the reaction was terminated. Then, absorption at 405 nm was measured using Color de Lys™ Developer and thereby evaluated as HDAC inhibitory activity. The strong HDAC inhibitor trichostatin A (TSA) was compared with SAHA and CTB in terms of HDAC inhibitory activity.

Figure 5:
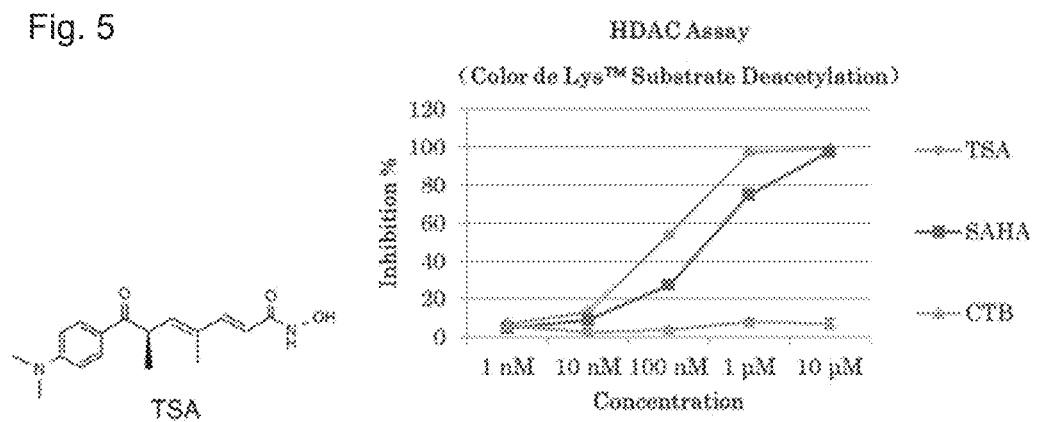
FIG. 5 is a drawing showing the structure of trichostatin A (TSA) and results of comparatively evaluating TSA, SAHA, and CTB for their HDAC inhibitory activity.

The results are shown in FIG. 5. From these results, CTB was confirmed to lack HDAC inhibitory activity.

Example 7

Cytotoxicity Assay

Cytotoxicity evaluation using the colorimetric method was conducted, as previously reported (Han, L. et al., Angew. Chem. Int. Ed. 2013, 52, 13410.), by using WST-8 (Dojindo Laboratories, Kumamoto, Japan) and 96-well plates and treating cells with varying concentrations of CTB or CTB-I.

Figure 6:
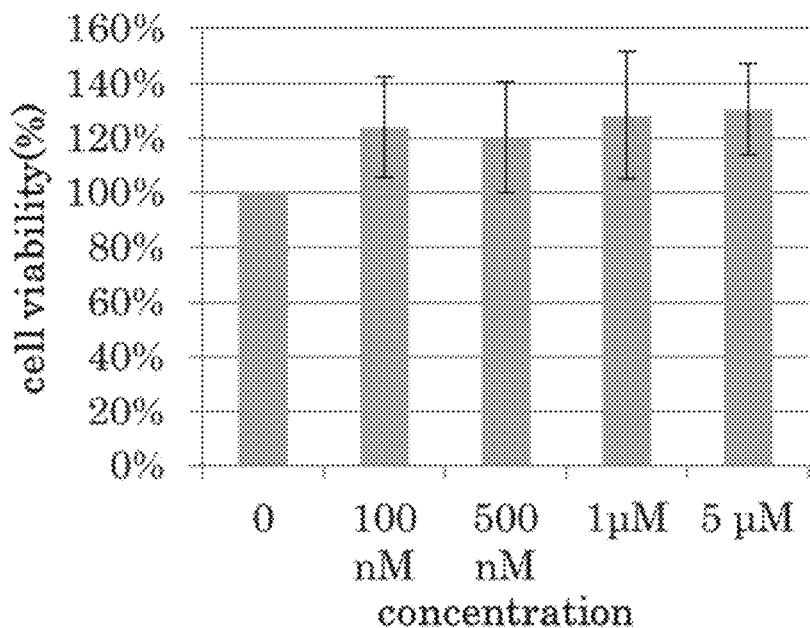
FIG. 6 is a drawing showing results of cytotoxicity assay on CTB and CTB-PIP-I.
Figure 6:
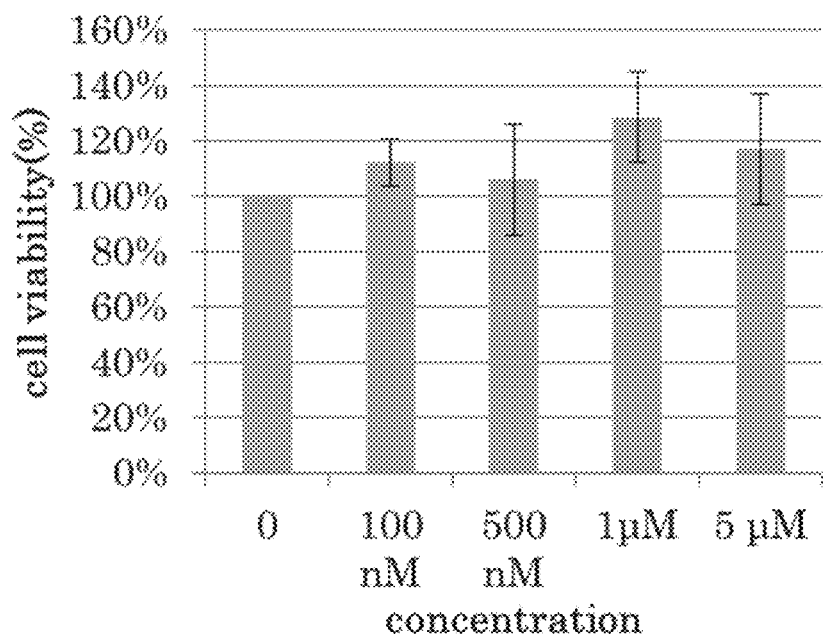

The results are shown in FIG. 6. These graphs suggest that cytotoxicity was not observed in both CTB and CTB-PIP-I up to, for example, concentrations equal to or lower than 5 µM.

Example 8

ChIP Sequencing Analysis

HDFs treated with CTB-PIP-I for 48 hours were immunoprecipitated. Then, the amount of the OCT-3/4 promoter sequence contained in coprecipitated DNA was measured. ChIP-seq experiment using an antibody against H3K14ac was conducted under the same conditions as previously described in Pandian, G. N. et al., ACS Chem. Biol. 2014, 10.1021/cb500724t, to examine acetylation mediated by CTB-PIP-I. Chip samples were mixed to obtain 50 to 100 ng in total of DNA. ChIP-Seq libraries were prepared using standard reagents of Ion Xpress™ Plus gDNA Fragment Library Preparation (Life Technologies Corp., USA) according to the protocol. The quality and quantity of the libraries were confirmed with Agilent DNA High sensitivity BioAnalyzer kit (Agilent Technologies, Inc., USA). Templates were prepared using a library that satisfied the conditions, Ion PGM™ template OT2 200 kit of Ion one touch 2, and Ion PI™ template OT2 200 kit. The templates were then enriched using Ion one touch ES. The enriched libraries were operated with a read length set to 100 nucleotides using Ion PGM sequencer and Ion PGM™ sequencing kit v2/318 chip or using Ion Proton™ sequencer and Ion PI™ Sequencing 200 kit/Ion PI chip according to the manual.

Typically, after filtration, 16,000,000 to 23,000,000 reads were obtained per library. Data was processed with the program package of Ion torrent suit. The reads were aligned using Torrent Mapping Alignment Program 3.4.3-1 (TMAP), and ChIP-Seq peaks were called using MACS 1.4.2 (Feng, J. et al., Nat. Protoc. 2012, 7, 1728).

Figure 7A:
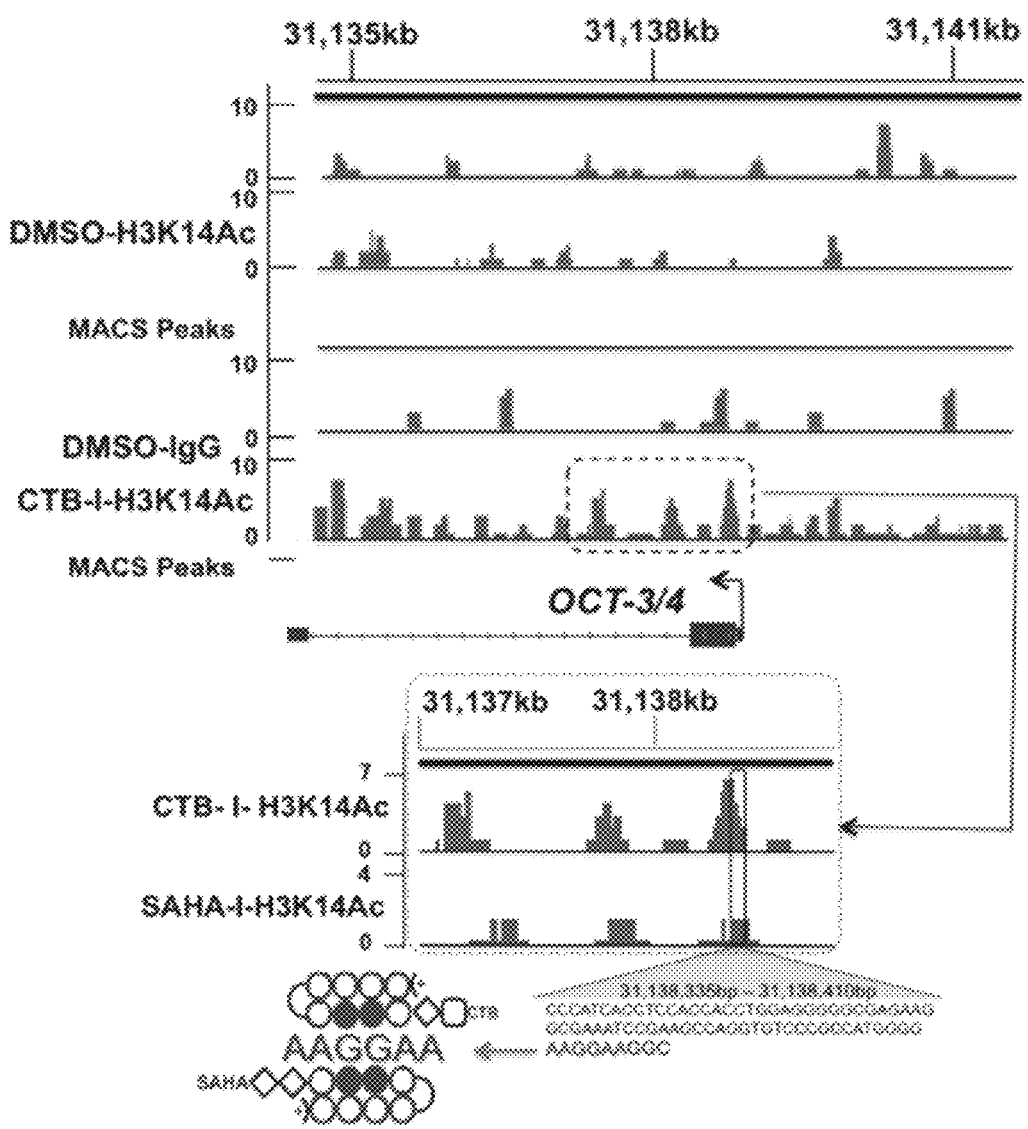
FIG. 7A is a drawing showing the acetylation peaks of SAHA-PIP-I and CTB-PIP-I in an Oct-3/4 gene promoter region in results of ChIP sequencing analysis after chromatin immunoprecipitation.
Figure 7B:
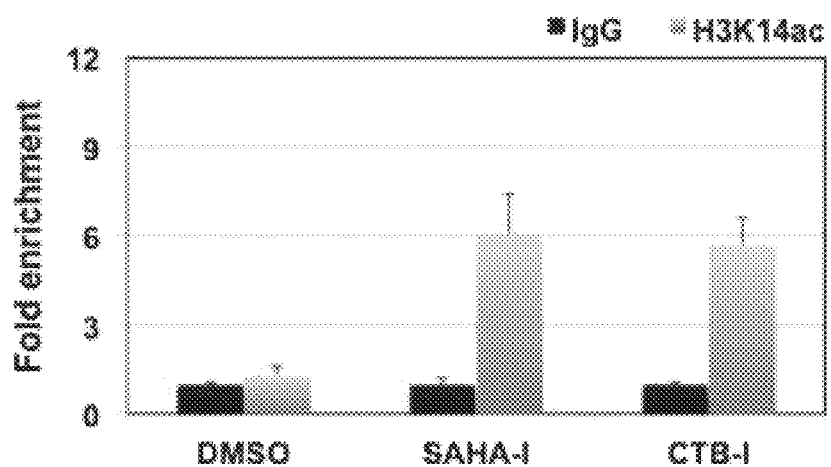
FIG. 7B is a drawing showing the amount of the Oct-3/4 promoter sequence in coprecipitated DNA.

The results are shown in FIGS. 7A and 7B. The results of ChIP sequencing analysis after chromatin immunoprscipitation are shown. It was confirmed by the ChIP sequencing analysis after immunoprecipitation that use of the antibody against H3K14ac induced the acetylation of histones binding to the Oct-3/4 gene promoter region. In the Oct-3/4 gene promoter region, both SAHA-PIP-I and CTB-PIP-I were observed to exhibit similar acetylation peaks (FIG. 7A). Also, SAHA-PIP-I and CTB-PIP-I were observed to result in the same level of the amount of the Oct-3/4 promoter sequence in coprecipitated DNA (FIG. 7B). In FIG. 7B, the right bars show the results about H3K14ac, and the left bars show the results about IgG. Particularly, the possibility is suggested that gene expression was inducted by the common specificity of SAHA-PIP-X and CTB-PIP-I for a sequence present in the Oct-3/4 gene promoter region (5'-AAGGAA-3') (SEQ ID NO: 21).

FIG. 8 shows a sequence related to the Oct-3/4 gene promoter region (SEQ ID NO: 22). In the information on a 1501-base sequence contained in this Oct-3/4 gene promoter region, there existed six 6-nucleotide sequences (5'-A/T-A/T-G-G-A/T-A/T-3') (SEQ ID NOs: 23 to 28) commonly recognized by SAHA-PIP-I and CTB-PIP-I. Association was observed between the positions of these recognized nucleotide sequences and the positions with activated histone acetyiation in the preceding ChIP sequence analysis.

|  |  |
|---|---|
| 5'-TAGGAA-3' | (SEQ ID NO: 23) |
| 5'-TTGGAA-3' | (SEQ ID NO: 24) |
| 5'-ATCCTA-3' | (SEQ ID NO: 25) |
| 5'-AACCAA-3' | (SEQ ID NO: 26) |
| 5'-TTGGAA-3' | (SEQ ID NO: 27) |
| 5'-AAGGAA-3' | (SEQ ID NO: 28) |

INDUSTRIAL APPLICABILITY

The "target gene-specific histone-modifying agent" of the present invention is expected as a drug that utilizes functional molecules activating gene expression, which are different from gene transfer methods such as viral vectors. This agent is also expected to be applied to, for example, tumor suppressor genes, viral disease suppressor genes, or genes (e.g., Sox and Klf) related to the maintenance, differentiation, or induction of stem cells or progenitor cells (e.g., iPS cells).

Free Text of Sequence Listing

SEQ ID NOs: 1 to 20 each represents a PCR primer.

SEQ ID NOs: 21 to 28 each represents a sequence in a promoter to which PIP-I binds by recognition.

The invention claimed is:
1. A conjugate selected from the group consisting of compounds represented by the formulae:
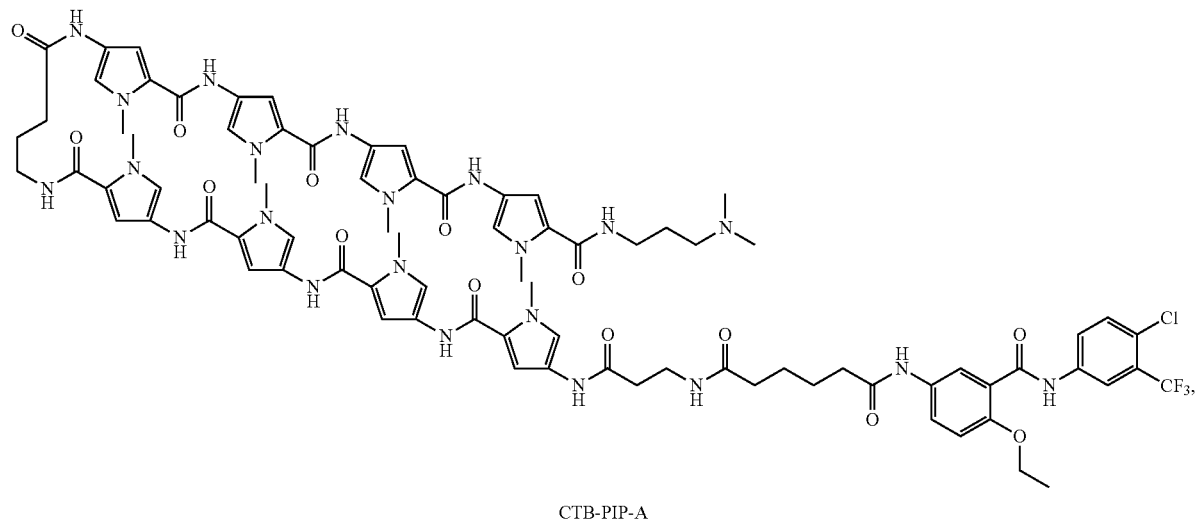
CTB-PIP-A
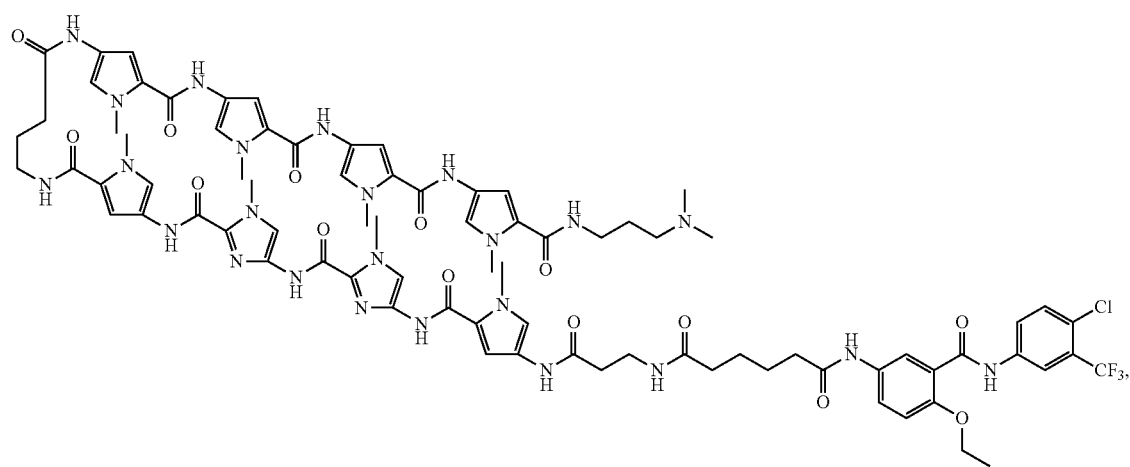
CTB-PIP-I
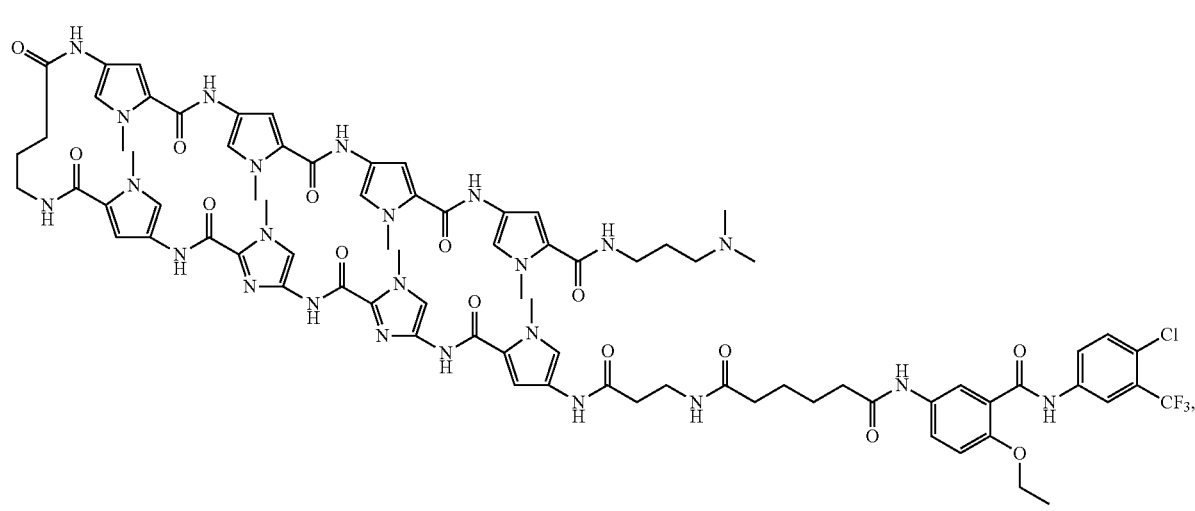
CTB-PIP-G

-continued

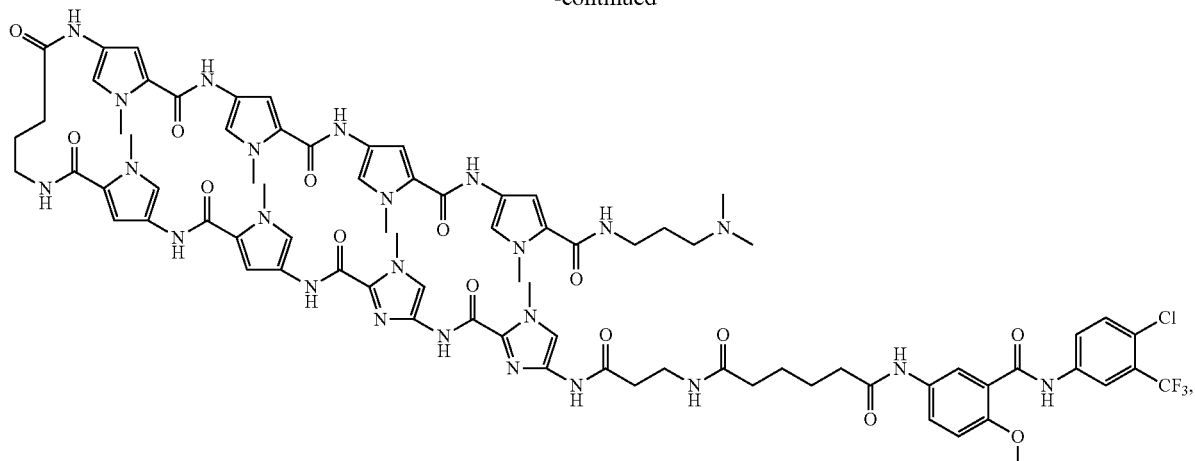

CTB-PIP-K

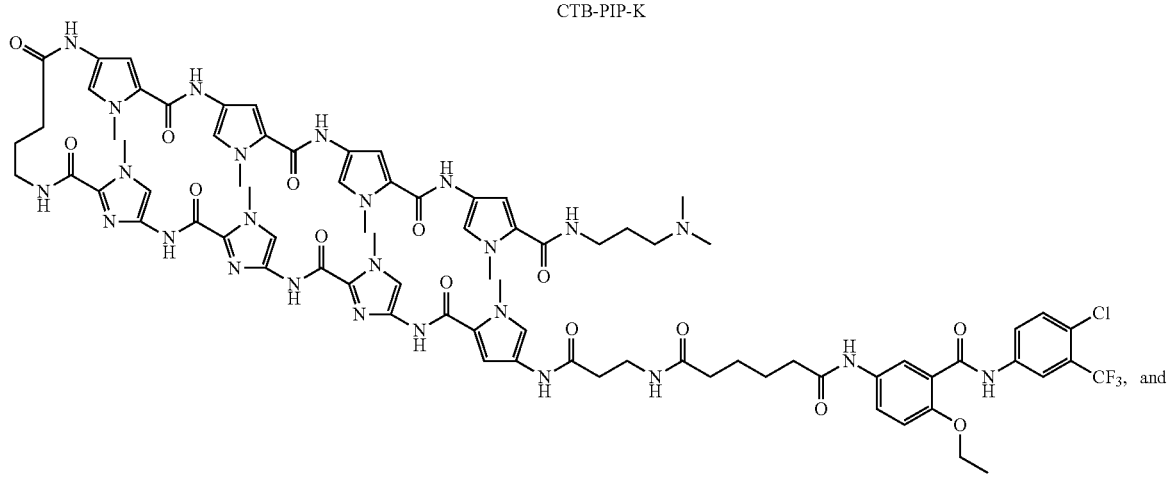

CTB-PIP-L

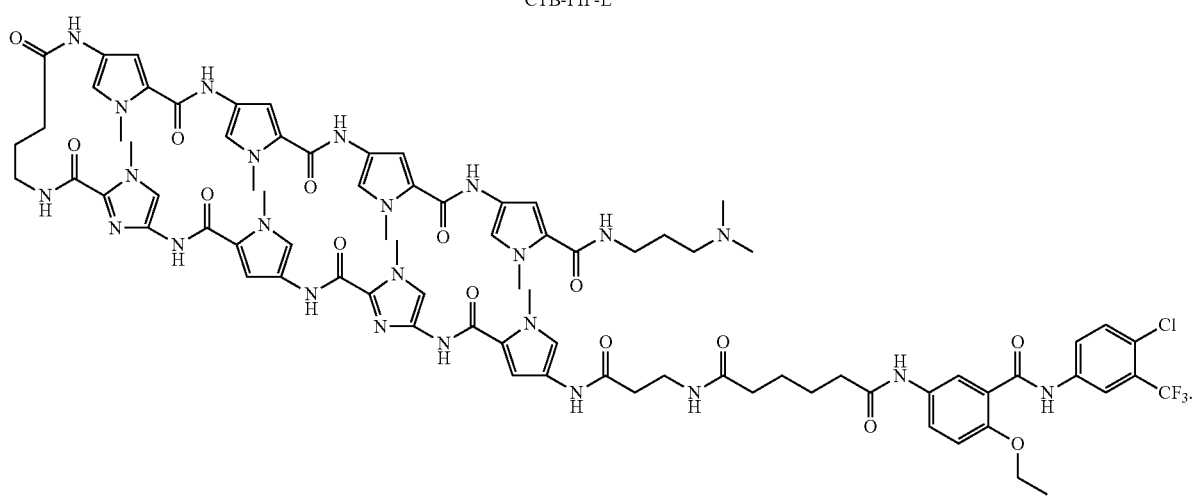

CTB-PIP-X

2. A pharmaceutical composition comprising the conjugate according to claim 1, and a pharmaceutically acceptable carrier or additive.

3. A kit for treatment or diagnosis or for research reagents, comprising the conjugate according to claim 1, and a carrier, additive, reagent, or auxiliary agent.

4. The kit according to claim 3 for the treatment or diagnosis of cancer or viral disease.

5. The pharmaceutical composition according to claim 2 for the treatment or diagnosis of cancer or viral disease.

* * * * *